(12) United States Patent
Webb et al.

(10) Patent No.: US 12,084,340 B2
(45) Date of Patent: Sep. 10, 2024

(54) MICRO-ELECTRO-MECHANICAL-SYSTEM STRUCTURES AND APPLICATIONS THEREOF

(71) Applicant: Mekonos, Inc., San Francisco, CA (US)

(72) Inventors: Mark A. Webb, Berkeley, CA (US); Luc Jan Bousse, Los Altos, CA (US); Arunava Steven Banerjee, San Mateo, CA (US)

(73) Assignee: Mekonos, Inc., San Francisco, CA (US)

( * ) Notice: Subject to any disclaimer, the term of this patent is extended or adjusted under 35 U.S.C. 154(b) by 453 days.

(21) Appl. No.: 17/617,917

(22) PCT Filed: Jun. 11, 2020

(86) PCT No.: PCT/US2020/037321
§ 371 (c)(1),
(2) Date: Dec. 9, 2021

(87) PCT Pub. No.: WO2020/252213
PCT Pub. Date: Dec. 17, 2020

(65) Prior Publication Data
US 2022/0306451 A1  Sep. 29, 2022

Related U.S. Application Data

(60) Provisional application No. 62/861,274, filed on Jun. 13, 2019.

(51) Int. Cl.
*B81B 1/00* (2006.01)

(52) U.S. Cl.
CPC .......... *B81B 1/002* (2013.01); *B81B 2203/04* (2013.01); *B81B 2207/015* (2013.01)

(58) Field of Classification Search
None
See application file for complete search history.

(56) References Cited

U.S. PATENT DOCUMENTS 5,114,854 A   5/1992   Bertholdt
5,262,128 A   11/1993  Leighton et al.
(Continued)

FOREIGN PATENT DOCUMENTS

CN   105441325   3/2016
CN   105967138   9/2016
(Continued)

OTHER PUBLICATIONS

Office Action issued in corresponding Canadian Application No. 3138947, dated Jan. 4, 2023.
(Continued)

*Primary Examiner* — Benjamin P Sandvik
(74) *Attorney, Agent, or Firm* — Norton Rose Fulbright US LLP

(57) ABSTRACT

A Micro-Electro-Mechanical-System (MEMS) device and a method for operating the device are disclosed. The device includes a substrate platform and an electrode plate having a plurality of serpentine arms, the electrode plate attached to the substrate platform via the plurality of serpentine arms, the electrode plate provided on a plane in a resting position. The device includes a sharp member disposed substantially perpendicularly on the electrode plate. In various implementations, the electrode plate and the substrate platform are co-planar. In various implementations, the electrode plate is configured to move in a direction perpendicular to the plane away from the resting position. The device also includes a counter-electrode. The method of operating the device includes supplying, via a power source, a direct current (DC) across the electrode and the counter-electrode to generate an electrostatic field across the electrode and the counter-electrode of the device.

20 Claims, 12 Drawing Sheets

(56) References Cited

U.S. PATENT DOCUMENTS

| | | | |
|---|---|---|---|
| 6,264,815 | B1 | 7/2001 | Pethig et al. |
| 6,475,760 | B1 | 11/2002 | Baumann et al. |
| 6,645,757 | B1 | 11/2003 | Okandan et al. |
| 7,501,276 | B2 | 3/2009 | Baumann et al. |
| 7,872,394 | B1 | 1/2011 | Gritters et al. |
| 9,987,427 | B1 | 6/2018 | Polsky et al. |
| 11,116,953 | B2 * | 9/2021 | Kobayashi ........ A61M 37/0015 |
| 2001/0008961 | A1 | 7/2001 | Hecker et al. |
| 2003/0015807 | A1 | 1/2003 | Montemagno et al. |
| 2004/0185592 | A1 | 9/2004 | Bergaud et al. |
| 2006/0072187 | A1 | 4/2006 | McKinnell et al. |
| 2007/0087436 | A1 | 4/2007 | Miyawaki et al. |
| 2007/0019422 | A1 | 8/2007 | Zorn |
| 2007/0194225 | A1 | 8/2007 | Zorn |
| 2007/0220882 | A1 | 9/2007 | Culpepper et al. |
| 2009/0166896 | A1 | 7/2009 | Yamazaki et al. |
| 2009/0198189 | A1 | 8/2009 | Simons et al. |
| 2009/0291502 | A1 | 11/2009 | Tateyama |
| 2011/0262891 | A1 | 10/2011 | Ozaki et al. |
| 2012/0225435 | A1 | 9/2012 | Seger et al. |
| 2013/0023052 | A1 | 1/2013 | Tanaka |
| 2013/0045530 | A1 | 2/2013 | Gracias et al. |
| 2013/0077945 | A1 | 3/2013 | Liu et al. |
| 2014/0323837 | A1 | 10/2014 | Hirshberg |
| 2016/0066789 | A1 | 3/2016 | Rogers et al. |
| 2016/0121092 | A1 | 5/2016 | Kato |
| 2016/0252546 | A1 | 9/2016 | Amponsah |
| 2019/0300907 | A1 | 10/2019 | Banerjee |
| 2020/0150141 | A1 | 5/2020 | Banerjee |
| 2021/0023356 | A1 * | 1/2021 | Kobayashi .............. B65B 5/045 |
| 2022/0306451 | A1 | 9/2022 | Webb et al. |

FOREIGN PATENT DOCUMENTS

| | | |
|---|---|---|
| CN | 110418844 | 11/2019 |
| EP | 1999465 | 11/2016 |
| EP | 2494332 | 8/2018 |
| EP | 3983054 | 12/2022 |
| JP | H 0660445 | 3/1994 |
| JP | A 1994060445 | 4/1994 |
| JP | A 2008072703 | 3/2008 |
| JP | A 2008516282 | 5/2008 |
| TW | 425294 | 3/2001 |
| WO | WO 2001/077001 | 10/2001 |
| WO | WO 2007/007058 | 1/2007 |
| WO | WO 2008/034249 | 3/2008 |
| WO | WO 2011/103143 | 8/2011 |
| WO | WO 2013/126556 | 8/2013 |
| WO | WO 2014/090415 | 6/2014 |
| WO | WO 2016/019250 | 2/2016 |
| WO | WO 2018/080324 | 5/2018 |
| WO | WO 2018/080325 | 5/2018 |
| WO | WO 2020252213 | 12/2022 |

OTHER PUBLICATIONS

Office Action issued in corresponding Chinese Application No. 202080042578.7, dated Feb. 3, 2023.
European Search Report issued in corresponding European Application No. 17864076.9, dated Jun. 3, 2020.
International Preliminary Report on Patentability issued in corresponding PCT Application No. PCT/NZ2017/050140, mailed May 9, 2019, 8 pages.
International Search Report issued in corresponding PCT Application No. PCT/NZ2017/050140, mailed on Feb. 19, 2011 pages.
International Search Report issued in corresponding PCT Application No. PCT/NZ2017/050140, mailed on Mar. 14, 2018, 17 pages.
Office Action issued in corresponding Australian Application No. 2017349494, dated Jan. 30, 2023.
Office Action issued in corresponding Australian Application No. 2020290475, dated Sep. 13, 2022.
Office Action issued in corresponding Chinese Application No. 2017800810960, dated Nov. 25, 2022.
Office Action issued in corresponding Chinese Application No. 201780080583.5, dated Nov. 25, 2022.
Office Action issued in corresponding Korean Application No. 10-2019-7015608, dated Feb. 23, 2022. (English Translation Provided).
Preliminary Report on Patentability issued in corresponding PCT Application No. PCT/NZ2017/050141, mailed May 9, 2019, 12 pages.
Republication (A9) of corresponding PCT Application No. PCT/NZ2017/050140, mailed Apr. 18, 2019, 87 pages.
Search Report and Written Opinion issued in corresponding Singapore Application No. 11201903750R, dated Jun. 23, 2020, 14 pages.
Search Report and Written Opinion issued in corresponding Singapore Application No. 11201903797S, dated Jul. 1, 2020, 9 pages.
Supplemental European Search Report issued in corresponding European Patent Application No. EP17863767.4, dated May 4, 2020, 8 pages.
International Search Report and Written Opinion issued in Corresponding PCT Application No. PCT/US2020/037321, dated Sep. 24, 2020.
Extended European Search Report issued in corresponding PCT Application No. 20822248.9, dated Jun. 27, 2022.

* cited by examiner

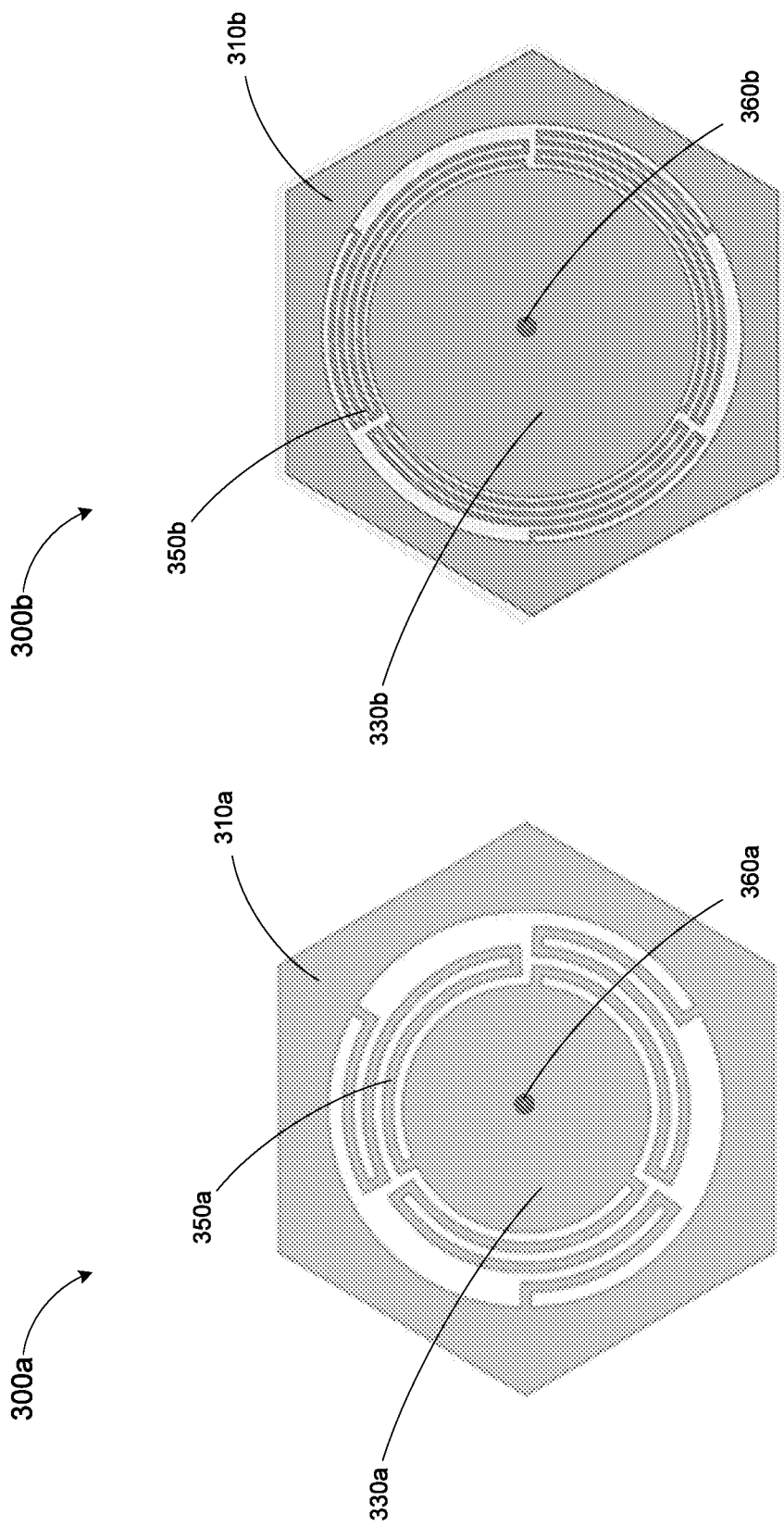

400 

410
Provide a power source

420
Provide a device comprising a substrate platform, an electrode having a plurality of serpentine arms, the electrode attached to the substrate platform via the plurality of serpentine arms, a sharp member disposed substantially perpendicularly on the electrode, and a counter-electrode disposed substantially parallel to the electrode;

430
Supply, via the power source, a direct current (DC) across the electrode and the counter-electrode of the device, thereby generating an electrostatic field across the electrode and the counter-electrode of the device

440
Supply, via the power source, an electric potential difference ($V_o$) between about 0.1 V and 10 kV across the electrode and the counter-electrode

450
Supply, via the power source, the direct current (DC) across each respective electrode and respective counter-electrode of a plurality of devices, thereby generating a plurality of electrostatic fields across each respective electrode and each respective counter-electrode of the plurality of devices

Figure 4

MICRO-ELECTRO-MECHANICAL-SYSTEM STRUCTURES AND APPLICATIONS THEREOF

CROSS-REFERENCE TO RELATED APPLICATIONS

The present application is a U.S. National Stage Patent Application of International Patent Application No. PCT/US2020/037321, filed on Jun. 11, 2020, which claims the benefit of U.S. Provisional Patent Application No. 62/861,274, filed on Jun. 13, 2019, the benefit of which is claimed and the disclosures of which are incorporated herein by reference in their entireties.

BACKGROUND

Medical treatment approaches, such as gene therapy via cellular transformations, are promising treatment options for a number of diseases, including inherited disorders, some types of cancer, and certain viral infections. Although gene therapy is promising, at present it is an experimental treatment based on insertion of genetic materials (genes) into a patient's cells instead of using drugs or surgery. Since the technique centers around introduction of genetic materials (or any biological molecules) into living cells, it is inherently risky and challenging, particularly for the danger of causing damage to the cells.

Current manufacturing approaches to gene therapy agents include, for example, an electroporation process where an application of a very high electric field to living cells to create transient openings in the membranes of the cells. The electric field is typically applied globally in a cuvette to a large number of cells, and neither the electrical field for a given cell, nor the amount of material that enters the cell is controlled for any individual cell. Another approach used for gene therapy is the use of a modified virus to introduce new genetic materials into cells. In this method, the presence of the virus can lead to many possible side-effects, including not being able to control what type of cells the virus will modify. Moreover, clinical applications of gene therapy with modified viruses have had serious side effects, including the development of cancer.

Since the above-mentioned techniques currently in use for cellular transformations and gene therapy have significant disadvantages, an alternative approach to inserting genetic materials into living cells is needed to advance a promising treatment technique, such as gene therapy, without harmful side effects present with the aforementioned approaches.

SUMMARY

At least one aspect of the disclosure is directed to a device. The device includes a substrate platform and a base plate having a plurality of serpentine arms, the base plate attached to the substrate platform via the plurality of serpentine arms, the base plate provided on a plane in a resting position. The device includes a sharp member disposed on the base plate, the sharp member disposed substantially perpendicular to the plane. In various implementations, the base plate and the substrate platform are co-planar. In various implementations, the base plate is configured to move in a direction perpendicular to the plane away from the resting position.

In various implementations, the base plate includes two serpentine arms that extend outwards from the base plate and are disposed radially evenly spaced from each other. In various implementations, the base plate includes three serpentine arms that extend outwards from the base plate and are disposed radially evenly spaced from each other. In various implementations, the base plate includes four serpentine arms that extend outwards from the base plate and are disposed radially evenly spaced from each other. In various implementations, the serpentine arms have a linear length at least about two times a separation distance between the base plate and the substrate platform. In various implementations, the serpentine arms have a linear length at least about three times or at least about four times a separation distance between the base plate and the substrate platform. In various implementations, the serpentine arms have a linear length up to about 1000 times a separation distance between the base plate and the substrate platform.

In various implementations, the base plate and the substrate platform are concentric. In various implementations, the base plate has a shape consisting of circular, oval, square, rectangle, pentagon, or hexagon. In various implementations, the base plate has a lateral dimension between about 100 nm and about 10 cm. In various implementations, the base plate has a lateral dimension between about 5 μm and about 500 μm.

In various implementations, the base plate moves from the resting position for a distance between about 0.1 nm and about 10 mm. In various implementations, the base plate moves from the resting position for a distance between about 1 nm and about 1 mm.

In various implementations, the base plate has a first thickness and the substrate platform has a second thickness. In various implementations, the first thickness differs from the second thickness. In various implementations, at least one of the base plate or the substrate platform has a thickness between about 0.001 μm and about 10 mm. In various implementations, at least one of the base plate or the substrate platform has a thickness between about 0.1 μm and about 10 μm.

In various implementations, at least one of the base plate or the substrate platform includes one of single crystal silicon, polycrystalline silicon, nanocrystalline silicon, amorphous silicon, or hydrogenated amorphous silicon.

In various implementations, at least one of the base plate or the substrate platform has a doping concentration between about $10^{10}$ atoms/cm$^3$ and about $10^{21}$ atoms/cm$^3$. In various implementations, at least one of the base plate or the substrate platform has a doping concentration between about $10^{11}$ atoms/cm$^3$ and about $10^{20}$ atoms/cm$^3$.

In various implementations, at least one of the base plate or the substrate platform has a sheet resistivity value between about $10^{-4}$ Ω-cm and about $10^4$ Ω-cm. In various implementations, at least one of the base plate or the substrate platform has a sheet resistivity value between about $10^{-3}$ Ω-cm and about $10^3$ Ω-cm. In various implementations, an electrical impedance across the base plate and the substrate platform is between about $10^2$Ω and about $10^{12}$Ω. In various implementations, an electrical impedance across the base plate and the substrate platform is between about $10^3$Ω and about $10^8$Ω.

In various implementations, the sharp member has a length between about 50 nm and about 1 mm. In various implementations, the sharp member has a length between about 2 μm and about 50 μm.

In various implementations, the sharp member is a first sharp member, and the device further includes a second sharp member. In various implementations, the device further includes a plurality of sharp members disposed on the base plate up to about 10 sharp members. In various implementations, the device further includes a plurality of sharp members disposed on the base plate up to about 100 sharp members. In various implementations, the device further includes a plurality of sharp members disposed on the base plate up to about 500,000,000 sharp members.

In various implementations, the base plate is a first base plate, the device further includes a second base plate. In various implementations, the device further includes a plurality of base plates.

In various implementations, the base plate is an electrode. In various implementations, the device further includes a counter-electrode disposed parallel to the electrode.

In various implementations, the counter-electrode has a thickness between about 0.001 μm and about 10 mm. In various implementations, the counter-electrode has a thickness between about 0.1 μm and about 10 μm.

In various implementations, the counter-electrode includes one of single crystal silicon, polycrystalline silicon, nanocrystalline silicon, amorphous silicon, hydrogenated amorphous silicon, indium-tin oxide (ITO), titanium nitride (TiN), a metal film, a doped semiconducting film, an inorganic semiconductor, a composite, an organic conducting film, or a carbon allotrope including various types of graphene, a graphene oxide, mismatched graphene, or any combination thereof.

In various implementations, the counter-electrode has a doping concentration between about $10^{10}$ atoms/cm$^3$ and about $10^{21}$ atoms/cm$^3$. In various implementations, the counter-electrode has a resistivity value between about $10^{-4}$ Ω-cm and about $10^4$ Ω-cm.

In various implementations, the electrode and the counter-electrode are configured to receive an electric potential difference ($V_o$) between about 0.1 μV and 10 kV. In various implementations, the electrode and the counter-electrode are configured to receive an electric potential difference ($V_o$) between about 1 V and 100 V. In various implementations, the electrode and the counter-electrode are configured to receive an electric potential difference ($V_o$) between about 10 V and 50 V.

In various implementations, a system includes a plurality of the devices as described above. In various implementations of the system, the plurality of devices ranges from about 1 to about $10^8$ devices, each of the devices having a respective sharp member. In various implementations of the system, the plurality of devices are separated from each other by between about 0.1 μm and 10 cm.

In various implementations, the counter-electrode has an opening at center of the counter-electrode and the opening is configured to receive a portion of the sharp member.

At least one aspect of the disclosure is directed to a method of operating a device. The method includes providing a power source and providing the device that includes a substrate platform and an electrode having a plurality of serpentine arms, the electrode attached to the substrate platform via the plurality of serpentine arms. In various implementations, the device also includes a sharp member disposed substantially perpendicularly on the electrode. In various implementations, the device also includes a counter-electrode disposed substantially parallel to the electrode. The method of operating the device also includes supplying, via the power source, a direct current (DC) across the electrode and the counter-electrode of the device to generate an electrostatic field across the electrode and the counter-electrode of the device.

In various implementations, the electrode and the substrate platform are co-planar. In various implementations, the electrode is provided on a plane in a resting position, and configured to move in a direction perpendicular to the plane away from the resting position.

In various implementations, the electrode includes two serpentine arms that extend outwards from the electrode and are disposed radially evenly spaced from each other. In various implementations, the electrode includes three serpentine arms that extend outwards from the electrode and are disposed radially evenly spaced from each other. In various implementations, the electrode includes four serpentine arms that extend outwards from the electrode and are disposed radially evenly spaced from each other.

In various implementations, the serpentine arms have a linear length at least about two times a separation distance between the electrode and the substrate platform. In various implementations, the serpentine arms have a linear length at least about three times a separation distance between the electrode and the substrate platform. In various implementations, the serpentine arms have a linear length at least about four times a separation distance between the electrode and the substrate platform. In various implementations, the serpentine arms have a linear length up to about 1000 times a separation distance between the electrode and the substrate platform.

In various implementations, the electrode and the substrate platform are concentric. In various implementations, the electrode has a shape consisting of circular disc, oval, square, rectangle, pentagon, or hexagon. In various implementations, the electrode has a lateral dimension between about 100 nm and about 10 cm. In various implementations, the electrode has a lateral dimension between about 5 μm and about 500 μm.

In various implementations, the electrode moves from the resting position for a distance between about 0.1 nm and about 10 mm. In various implementations, the electrode moves from the resting position for a distance between about 1 nm and about 1 mm.

In various implementations, the electrode has a first thickness and the substrate platform has a second thickness. In various implementations, the first thickness differs from the second thickness. In various implementations, at least one of the electrode or the substrate platform has a thickness between about 0.001 μm and about 10 mm. In various implementations, at least one of the electrode or the substrate platform has a thickness between about 0.1 μm and about 10 μm.

In various implementations, at least one of the electrode or the substrate platform includes one of single crystal silicon, polycrystalline silicon, nanocrystalline silicon, amorphous silicon, or hydrogenated amorphous silicon.

In various implementations, at least one of the electrode or the substrate platform has a doping concentration between about $10^{10}$ atoms/cm$^3$ and about $10^{21}$ atoms/cm$^3$. In various implementations, at least one of the electrode or the substrate platform has a doping concentration between about $10^{11}$ atoms/cm$^3$ and about $10^{20}$ atoms/cm$^3$. In various implementations, at least one of the electrode or the substrate platform has a resistivity value between about $10^{-4}$ Ω-cm and about $10^4$ Ω-cm. In various implementations, at least one of the electrode or the substrate platform has a resistivity value between about $10^{-3}$ Ω-cm and about $10^3$ Ω-cm. In various implementations, an electrical impedance across the electrode and the substrate platform is between about $10^2 Ω$ and about $10^{12} Ω$. In various implementations, an electrical impedance across the electrode and the substrate platform is between about $10^3 Ω$ and about $10^8 Ω$.

In various implementations, the sharp member has a length between about 50 nm and about 1 mm. In various implementations, the sharp member has a length between about 2 µm and about 50 µm.

In various implementations, the sharp member is a first sharp member, the device further includes a second sharp member. In various implementations, the device further includes a plurality of sharp members up to about 10 sharp members. In various implementations, the device further includes a plurality of sharp members up to about 100 sharp members. In various implementations, the device further includes a plurality of sharp members up to about 500,000,000 sharp members.

In various implementations, the electrode is a first electrode, and the device further includes a second electrode. In various implementations, the device further includes a plurality of electrodes.

In various implementations, the counter-electrode has a thickness between about 0.001 µm and about 10 mm. In various implementations, the counter-electrode has a thickness between about 0.1 µm and about 10 µm.

In various implementations, the counter-electrode includes one of single crystal silicon, polycrystalline silicon, nanocrystalline silicon, amorphous silicon, hydrogenated amorphous silicon, indium-tin oxide (ITO), titanium nitride (TiN), a metal film, a doped semiconducting film, an inorganic semiconductor, a composite, an organic conducting film, a carbon allotrope including various types of graphene, a graphene oxide, mismatched graphene, and any combination thereof.

In various implementations, the counter-electrode has a doping concentration between about $10^{10}$ atoms/cm$^3$ and about $10^{21}$ atoms/cm$^3$. In various implementations, the counter-electrode has a resistivity value between about $10^{-4}$ Ω-cm and about $10^4$ Ω-cm.

In various implementations, the method further includes supplying, via the power source, an electric potential difference ($V_o$) between about 0.1 µV and 10 kV across the electrode and the counter-electrode.

In various implementations, the method further includes supplying, via the power source, an electric potential difference ($V_o$) between about 1 V and 100 V across the electrode and the counter-electrode. In various implementations, the method further includes supplying, via the power source, an electric potential difference ($V_o$) between about 10 V and 50 V across the electrode and the counter-electrode.

In various implementations, the device is a first device, the method further includes a plurality of devices, and supplying, via the power source, the direct current (DC) across each respective electrode and respective counter-electrode of the plurality of devices to generate a plurality of electrostatic fields across each respective electrode and each respective counter-electrode of the plurality of devices.

In various implementations, the plurality of devices ranges from about 1 to about $10^8$ devices, each of the devices having a respective sharp member. In various implementations, the plurality of the devices are separated from each other by between about 0.1 µm and 10 cm.

In various implementations, the counter-electrode has an opening at center of the counter-electrode and the opening is configured to receive a portion of the sharp member.

At least one aspect of the disclosure is directed to a component. The component includes a substrate platform and an electrode plate having a plurality of serpentine arms, the electrode plate attached to the substrate platform via the plurality of serpentine arms, the electrode plate provided on a plane in a resting position. In various implementations, the electrode plate and the substrate platform are co-planar. In various implementations, the electrode plate is configured to move in a direction perpendicular to the plane away from the resting position.

In various implementations, the component further includes a sharp member disposed on the electrode plate. In various implementations, the electrode plate and the substrate platform are concentric, and the plurality of serpentine arms extend from the electrode plate to the substrate platform.

In various implementations, at least a portion of the plurality of serpentine arms is co-planar with either the electrode plate or the substrate platform. In various implementations, the plurality of serpentine arms are radially evenly spaced from each other.

In various implementations, the plurality of serpentine arms range from about two arms to about ten arms. In various implementations, the serpentine arms have a linear length at least about two times a separation distance between the electrode plate and the substrate platform. In various implementations, the serpentine arms have a linear length at least about four times a separation distance between the electrode plate and the substrate platform. In various implementations, the serpentine arms have a linear length up to about 1000 times a separation distance between the electrode plate and the substrate platform.

In various implementations, the electrode plate moves away from the plane for a distance between about 1 µm and about 10 mm. In various implementations, the electrode plate moves away from the plane for a distance between about 10 µm and about 1 mm. In various implementations, the electrode plate has a shape consisting of circular disc, oval, square, rectangle, pentagon, or hexagon.

In various implementations, the electrode plate has a lateral dimension between about 100 nm and about 10 cm. In various implementations, the electrode plate has a lateral dimension between about 5 µm and about 500 µm. In various implementations, the electrode plate has a first thickness and the substrate platform has a second thickness. In various implementations, the first thickness differs from the second thickness.

In various implementations, at least one of the electrode plate or the substrate platform has a thickness between about 0.001 µm and about 10 mm. In various implementations, at least one of the electrode plate or the substrate platform has a thickness between about 0.1 µm and about 10 µm.

In various implementations, at least one of the electrode plate or the substrate platform includes one of single crystal silicon, polycrystalline silicon, nanocrystalline silicon, amorphous silicon, or hydrogenated amorphous silicon.

In various implementations, at least one of the electrode plate or the substrate platform has a doping concentration between about $10^{10}$ atoms/cm$^3$ and about $10^{21}$ atoms/cm$^3$. In various implementations, at least one of the electrode plate or the substrate platform has a doping concentration between about $10^{11}$ atoms/cm$^3$ and about $10^{20}$ atoms/cm$^3$.

In various implementations, at least one of the electrode plate or the substrate platform has a resistivity value between about $10^{-4}$ Ω-cm and about $10^4$ Ω-cm. In various implementations, at least one of the electrode plate or the substrate platform has a resistivity value between about $10^{-3}$ Ω-cm and about $10^3$ Ω-cm. In various implementations, an electrical impedance across the electrode plate and the substrate platform is between about $10^2$Ω and about $10^{12}$Ω. In various implementations, an electrical impedance across the electrode plate and the substrate platform is between about $10^3$Ω and about $10^8$Ω.

In various implementations, the sharp member has a length between about 50 nm and about 1 mm. In various implementations, the sharp member has a length between about 2 µm and about 50 µm.

In various implementations, the sharp member is a first sharp member, the device further comprising a second sharp member. In various implementations, the component further includes a plurality of sharp members up to about 10 sharp members. In various implementations, the component further includes a plurality of sharp members up to about 100 sharp members. In various implementations, the component further includes a plurality of sharp members up to about 500,000,000 sharp members.

In various implementations, the electrode plate is a first electrode plate, the component further includes a second electrode plate. In various implementations, the component further includes a plurality of electrode plates.

In various implementations, the component further includes a counter-electrode disposed substantially parallel to the electrode plate.

In various implementations, the counter-electrode has a thickness between about 0.001 µm and about 10 mm. In various implementations, the counter-electrode has a thickness between about 0.1 µm and about 10 µm.

In various implementations, the counter-electrode includes one of single crystal silicon, polycrystalline silicon, nanocrystalline silicon, amorphous silicon, hydrogenated amorphous silicon, indium-tin oxide (ITO), titanium nitride (TiN), a metal film, a doped semiconducting film, an inorganic semiconductor, a composite, an organic conducting film, a carbon allotrope including various types of graphene, a graphene oxide, mismatched graphene, and any combination thereof.

In various implementations, the counter-electrode has a doping concentration between about $10^{10}$ atoms/cm$^3$ and about $10^{21}$ atoms/cm$^3$. In various implementations, the counter-electrode has a doping concentration between $10^{11}$ atoms/cm$^3$ and about $10^{20}$ atoms/cm$^3$. In various implementations, the counter-electrode has a resistivity value between about $10^{-4}$ Ω-cm and about $10^4$ Ω-cm.

In various implementations, the electrode and the counter-electrode are configured to receive an electric potential difference (Vo) between about 0.1 µV and 10 kV. In various implementations, the electrode and the counter-electrode are configured to receive an electric potential difference (Vo) between about 1 V and 100 V. In various implementations, the electrode and the counter-electrode are configured to receive an electric potential difference (Vo) between about 10 V and 50 V.

In various implementations, a system includes a plurality of components as described above. In various implementations the system, the plurality of components ranges from about 1 to about $10^8$ components, each of the components comprising a respective sharp member. In various implementations of the system, the plurality of components are separated from each other by between about 0.1 µm and 10 cm.

In various implementations, the counter-electrode has an opening at center of the counter-electrode and the opening is configured to receive a portion of a sharp member disposed on the electrode plate.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 3A shows a schematic top view of another example MEMS structure having serpentine arms, according to various implementations;

FIG. 3B shows a schematic top view of yet another example MEMS structure having serpentine arms, according to various implementations;

FIG. 4 is a flow chart for a method of operating an example MEMS device having serpentine arms, according to an illustrative implementation.

DETAILED DESCRIPTION

Figure 1A:
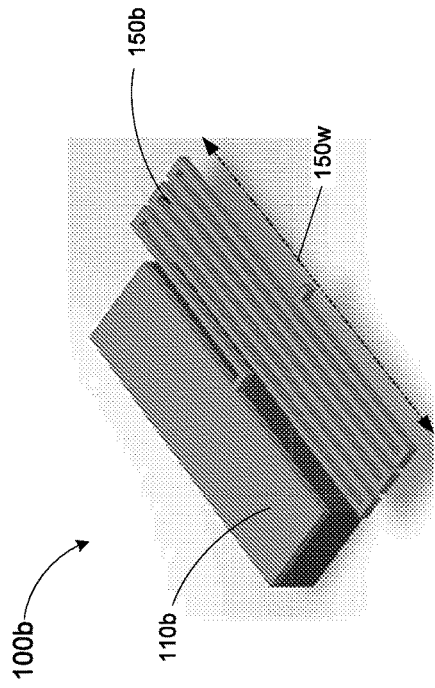
FIG. 1A shows a schematic view of a simple cantilever structure.

The technology described herein enables a safer approach to inserting genetic materials. The disclosed technology can enable controllable introduction of genetic materials (biological molecules in general) into living cells by mechanical means, while causing minimal or no damage to the cells so that a high percentage of the cells are unharmed. Example genetic materials can include, for example, genetic macromolecules as well as other molecule classes that include, for example, proteins, peptides, small molecules, protein complexes with RNAs or DNAs, and any combinations thereof. Significant advantages with the use of a mechanical insertion include having a precise mechanical control of the insertion tool, in addition to controlling the precise amount of active molecules, for example, new genetic materials, that are to be transported by the mechanical tool.

It is well known that Micro-Electro-Mechanical-System (MEMS) based fabrication technologies can enable manufacturing of microscopic components, such as the mechanical tool that can be used for cell interrogation. MEMS based fabrication methods are particularly suited to produce microscopically sharp tools, for example needles (referred to herein as micro-needles or nano-needles) that can be used in gene therapy, among other possible applications. It has been shown that needles (MEMS based or otherwise) can be used for inserting molecular materials into biological cells, such as epidermal layers or layers of cultured adherent cells. These types of insertions are typically conducted by manually pressing a needle into a cell or a layer of epidermal tissue.

However, currently available approaches employing a mechanical insertion are not integrated with any kind of actuation mechanism, and there is no individual control of the position of the insertion needle relative to the cell to be injected. In currently available approaches used in cellular modification, the insertion system does not include an actuation mechanism for the needle, and the insertion needle is manually pressed into the target cell by a technician. Since the movement of the insertion needle is manually controlled by the technician, a precise control of the height of each individual needle is difficult to achieve as it penetrates the target cell. In addition, since the technician carries out the insertion, the insertion of the genetic materials into the cell is done individually and automation capability is lacking. As such, the current approach does not offer scalability in the mechanical approach of gene therapy.

One possible solution to improve the control and scalability aspects of the mechanical approach to gene therapy is to use MEMS based fabrication methods to fabricate many sharp tools that are each mounted on a platform that is capable of supporting a mechanism for precise actuation of the sharp tools. If the MEMS based sharp tools, such as needles, offer precise control of their mechanical movements via the integrated actuation mechanism, a high-throughput and perhaps parallel approach to gene therapy can be achieved with the technology as described herein.

The technology described herein generally relates to MEMS structures and applications thereof. In particular, the disclosure relates to a MEMS structure having a sharp tool, such as a MEMS needle (including a solid tip or a hollow tip), disposed thereon and a method of operating the structure suitable for used in, for example, but not limited to, gene therapy and/or cellular transformations. Specifically, the disclosure relates to a MEMS structure (can also refer to as a MEMS device or a MEMS component) with a compact actuation mechanism having ultralow spring constant and precise actuation. Various implementations of the MEMS structure as described herein are fabricated using micro- and nanofabrication technologies, including, but not limited to, photolithography, vapor deposition and plasma etching, etc. Since MEMS based fabrication methods generally involve photolithography, scaling to produce hundreds of thousands of components or devices can be readily accomplished simply by modifying a photolithographic mask in the fabrication process flow. Although referred to herein as MEMS structures, since the disclosed technology also includes fabrication of nanometer scale structures, components or devices, the term MEMS structure also refers to Nano-Electro-Mechanical System (NEMS) structure, and accordingly, the terms MEMS and NEMS are interchangeable and applicable to various implementations and embodiments throughout the disclosure, unless otherwise specified differently.

As described herein, the MEMS structure or device includes a substrate platform and a base plate having a plurality of serpentine arms, the base plate attached to the substrate platform via the plurality of serpentine arms, the base plate provided on a plane in a resting position. The device includes a sharp member disposed on the base plate, the sharp member disposed substantially perpendicular to the plane away from the resting position. In various implementations, the base plate and the substrate platform are co-planar. In various implementations, the base plate is configured to move in a direction perpendicular to the plane. In various implementations, the base plate includes at least two serpentine arms that extend outwards from the base plate and are disposed radially evenly spaced from each other. In various implementations, the serpentine arms are configured so that the spring constant is low and precisely controlled to enable compact yet precise actuation.

In order to utilize the MEMS structure for gene therapy, for example, in in-vitro cellular transformation, cells are typically collected, selected, and held in place (otherwise suspended in place) prior to insertion. Various implementations described herein include a mechanical insertion method using a MEMS needle (generally referred to herein as a sharp tool or sharp member) that on the scale of cellular dimensions, i.e., in the nanometer range. For the desired precision and controllability, the disclosed MEMS needle (or generally as a needle) is to be coupled to an actuation mechanism that moves the needle such that it penetrates the cellular membrane and, for example, also the nuclear membrane of eukaryotic cells. The specified movement of the MEMS needle and as well as its actuation mechanism as described herein are as follows: The needle is sharp enough to penetrate the cellular membrane and the nuclear membrane with minimal force and minimal disruption to the cell outside the penetration point; the needle is capable of being actuated over a sufficient distance, typically in the order of the cell dimensions, i.e., from about 2 µm to about 20 µm, and preferably from about 4 µm to about 8 µm; the needle has an individual actuation mechanism that enables accurate movement relative to the cell that is being held in place; and the actuation mechanism for each of the MEMS needles is compact so that the total area of the needle and its actuation mechanism is small. In various implementations as described herein, the MEMS devices, which include both the needles and actuation mechanism, have above-mentioned device parameters and are to be numbered in excess of 100 devices per square-centimeter (devices/cm$^2$), preferably in excess of 1000 devices/cm$^2$, or up to about 10,000 devices, about 50,000 devices, about 100,000 devices, about 500,000 devices, about 1,000,000 devices, about 5,000,000 devices, about 10,000,000 devices, about 50,000,000 devices, about 100,000,000 devices, or about 500,000,000 devices, including any range of number of devices between any two numbers described above.

According to various implementations as described herein, the disclosed MEMS structures can be actuated via any suitable actuation approach, including electrostatic actuation of the MEMS structures. Other suitable actuation approaches can also be used for actuation. For example, piezoelectric components that move in response to externally applied voltages can be used for actuation. Magnetic forces can also be used in several ways by attaching magnets to the actuators, that can be moved upon exerting an external magnetic field. Similarly, the actuation of the MEMS structures can be done based on temperature differences, such as by employing bimetallic elements or those based on shape memory alloys. The temperatures needed for actuation can be generated by fabricated resistive heaters in selected locations of the device.

Although the electrostatic actuation is used throughout the disclosure as an example approach for actuating of the disclosed MEMS structures, the technology described herein is not limited to electrostatic actuation, and the MEMS structures can therefore be used with any form of actuation in accordance with the technology disclosed herein.

For use with electrostatic actuation, the MEMS structures are configured to include electrical contact pads for an electrostatic actuation mechanism. The electrostatic actuation offers several advantages. One major advantage is provided by the configuration of parallel plate electrostatic actuation device architecture, which requires minimal lithographic layers and processing steps in manufacturing of the structures. Another advantage relates to a large range of motion associated with electrostatically actuated motion, which is determined by the specific configuration of the MEMS structure and the applied voltage. Another advantage is that the components of the MEMS structures themselves can be configured as the electrical conductors, which therefore eliminates the need for additional elements, such as magnets, coils, or piezoelectric materials that are needed if any of those actuation mechanisms are employed. For electrostatic actuation, the possibility to convert any of the MEMS components that are made of silicon into electrical conductors by simply doping the components offers a unique ability to engineer various parts of the MEMS structures.

According to various implementations as described herein, the disclosed MEMS structure includes a spring or a spring-like flexible structure that allows the MEMS needle to move when an actuation force is applied, and generates a restoring force that returns the MEMS needle to its initial resting position when the actuation force is removed. To determine spring constant values suitable for use in this application can be related via the following two equations. The first equation that describes an electrostatic actuation force that results when an electric potential voltage is applied across two plates of a parallel-plate capacitor can be described as:

$$F = \frac{\varepsilon A}{2} \frac{V^2}{d^2}$$

where A is the area of the plates (with one plate having the MEMS needle disposed thereon), d the separation distance between the two parallel plates, V the voltage applied, and ε is the permittivity of free space. By inserting typical orders of magnitude for these variables, such as a 100 μm by 100 μm MEMS structural surface area, a 10 μm separation distance, and an applied voltage of 50 V, it can be seen that forces on the order of 1 μN can be generated. Since the MEMS needle is on the order of 10 μm, a spring constant on the order of 0.1 N/m is needed to enable proper actuation of the MEMS needle.

FIG. 1A shows a schematic view of a simple cantilever structure 100a used for determining the dimensions of a cantilever beam 150a that has a spring constant k on the order of 0.1 N/m. As shown in FIG. 1A, the cantilever beam 150a is suspended from a substrate platform 110a, where the dimensions of the cantilever beam 150a is related to its spring constant k via the second equation, which is based on a singly clamped cantilever beam theory, as:

$$k = E\frac{WH^3}{L^3}$$

where E is Young's modulus, W the width, H the height, and L the length of the cantilever beam. For example, for a cantilever beam 150a made of single crystal silicon with a typical height of 2 mm and a width of 5 μm, a silicon beam 150a of 100 μm in length is determined to have a spring constant 6 N/m according to the second equation. The spring constant of 6 N/m is much stiffer than the spring constant of 0.1 N/m needed to enable proper actuation of the MEMS needle at an applied voltage of 50 V. In order to reduce the spring constant to about 0.1 N/m, the silicon cantilever beam will have to have a length of about 500 μm, assuming that there are at least two cantilever beams needed to provide a stable support of each MEMS needle. The total dimension of the device, as a result, would exceed 1000 μm, which is 10 times larger or longer than the 100 μm by 100 μm MEMS structure that the two 500-μm cantilevers are configured to support.

According to various implementations as described herein, the solution is for the disclosed MEMS structures to include springs or spring-like structures that are different than the straight beam shown in FIG. 1A. The springs or spring-like structures, can include, for example, serpentine like beam structures. The serpentine structures attached to the MEMS structures offer lower spring constants while being compact by effectively folding a long cantilever beam into a compact serpentine pattern to form serpentine structures (referred to herein generally as serpentine arms). Other possible geometries of springs or spring-like structures include, for example, a set of spiral shaped springs that are long, compact, and flexible. In various implementations, the set of spiral shaped springs may not be serpentine or meandering.

Figure 1B:
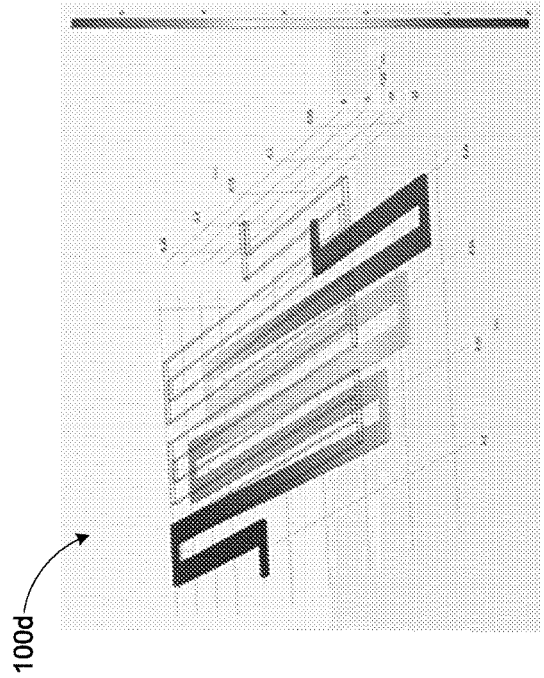
FIG. 1B shows a schematic view of a serpentine cantilever structure, according to various implementations.

FIG. 1B shows a schematic view of a serpentine cantilever structure 100b, according to various implementations. As shown in FIG. 1B, the structure 100b includes a serpentine cantilever beam 150b having a width 150w attached to a substrate platform 110b. The serpentine cantilever beam 150b is configured to significantly reduce its stiffness, i.e., lower its spring constant. The serpentine structure 150b has a much longer linear (effective) length that is folded to decrease the actual distance between the tip of the serpentine cantilever beam 150b and the base of the serpentine cantilever beam 150b, where the cantilever beam 150b is attached to the substrate platform 110b.

Figure 1C:
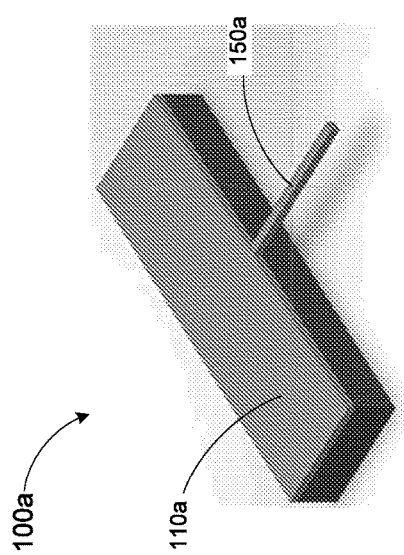
FIG. 1C is a graphical illustration of stiffness reduction as a function of the serpentine cantilever structure widths in FIG. 1B.

FIG. 1C is a graphical plot 100c showing stiffness reduction as a function of the serpentine cantilever structure width 150w in FIG. 1B. As shown in FIG. 1C, the stiffness of the cantilever beam 150a shown in FIG. 1A can decrease if a serpentine structure is included in the beam structure as shown in the serpentine cantilever beam 150b of FIG. 1B. According to the relationship illustrated in FIG. 1C, the stiffness is reduced exponentially as the serpentine cantilever structure width 150w increases, and therefore large ratios of reduction in stiffness can easily be achieved by having a modest serpentine width 150w in the beam structure. In other words, the plot 100c illustrates that a more compliant and compact cantilever arm structures (springs) can be engineered by inclusion of the serpentine structures in the cantilever beams.

Figure 1D:
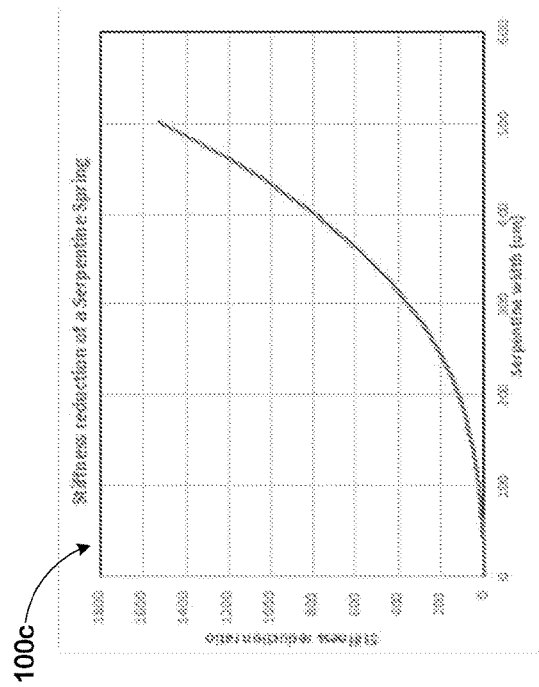
FIG. 1D is a graphical illustration showing simulation results of a serpentine cantilever structure being deflected.

FIG. 1D is a graphical illustration 100d showing simulation results of the serpentine cantilever structure 100b being deflected. As shown in FIG. 1D, the finite element simulation of the serpentine cantilever structure 100b demonstrates the ability of the serpentine flexures to achieve deflections considerably higher than the thickness of the cantilever structure. The downward deflection shown in the illustration 100d illustrates and verifies that having the serpentine structure in the cantilever structure 100b enables a much higher compliance due to a lower spring constant enabled by a much longer effective length of the structure 100b.

Figure 2A:
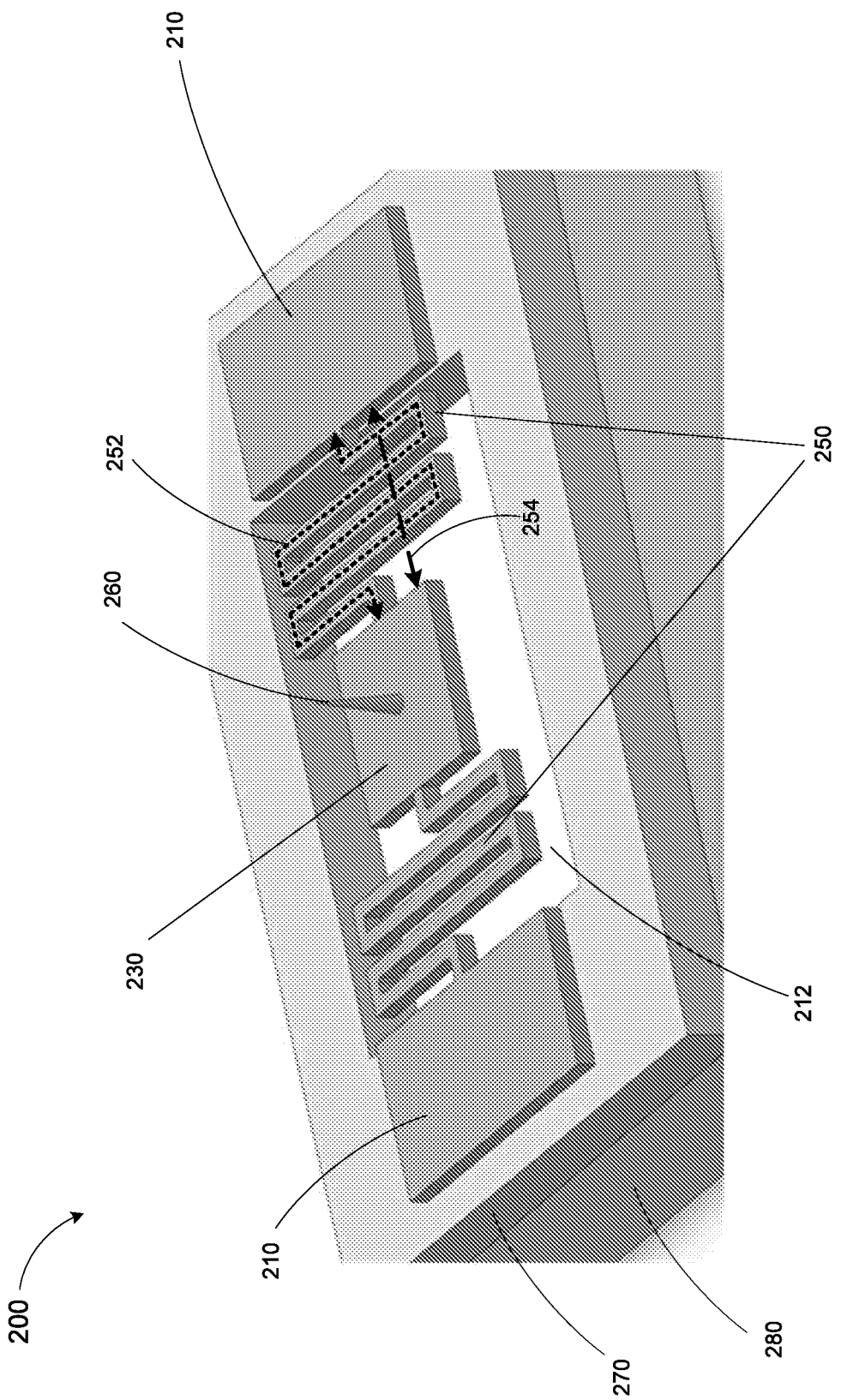
FIG. 2A shows a schematic view of an example MEMS structure having serpentine arms, according to various implementations.

FIG. 2A shows a schematic view of an example MEMS structure 200 having serpentine arms, according to various implementations as disclosed herein. As shown in FIG. 2A, the structure 200 includes a substrate platform 210 and a base plate 230 having a plurality of serpentine arms 250. As shown in FIG. 2A, the base plate 230 is attached to the substrate platform 210 via the plurality of serpentine arms 250 so that the base plate 230 is at a resting position above a pit 212. The structure 200 includes a sharp member 260 disposed on the base plate 230. As shown in FIG. 2A, the sharp member 260 is disposed substantially perpendicular to the plane of the base plate 230. Initially, the base plate and the substrate platform are co-planar. In various implementations, the base plate 230 is an electrode and is configured to move up or down away from the resting position based on electrostatic actuation in a direction perpendicular to the base plate 230 and the substrate platform 210. Also visible are the substrate 270 and bottom electrode or counter electrode 280.

In various implementations, the substrate platform 210 includes one of single crystal silicon, polycrystalline silicon, nanocrystalline silicon, amorphous silicon, or hydrogenated amorphous silicon. In various implementations, the substrate platform 210 can include a metal, a metallic alloy, a ceramic, a composite, or a polymer. In various implementations, the substrate platform 210 can include doped silicon, any allotrope of silicon, any inorganic glassy material or mixture, any inorganic polycrystalline material or mixture, any inorganic single crystalline material or mixture, any ceramic material comprising metal oxides, metalloid oxides, metal or metalloid nitrides, metal or metalloid oxides with nitrogen or other non-metalloid or metal elements, any doped combination of the above materials, any layered stack or structural combination of the above materials.

In various implementations, the substrate platform 210 is a single layer of materials. In various implementations, the substrate platform 210 is a composite material having multiple layers. In various implementations, the substrate platform 210 can include an empty void layer, or one or more voids in the composite material.

In various implementations, the substrate platform 210 has a thickness between about 0.001 µm and about 10 mm. In various implementations, the substrate platform 210 has a thickness between about 0.01 µm and about 1 mm, about 0.01 µm and about 500 µm, about 0.01 µm and about 100 µm, about 0.01 µm and about 75 µm, about 0.01 µm and about 50 µm, about 0.01 µm and about 25 µm, about 0.01 µm and about 10 µm, about 0.1 µm and about 10 µm, about 0.1 µm and about 25 µm, about 0.1 µm and about 50 µm, about 0.1 µm and about 75 µm, about 0.1 µm and about 100 µm, about 0.1 µm and about 250 µm, about 0.1 µm and about 500 µm, or about 0.1 µm and about 1 mm, inclusive of any thickness ranges therebetween.

In various implementations, the substrate platform 210 has a doping concentration between about $10^{10}$ atoms/cm³ and about $10^{21}$ atoms/cm³. In various implementations, the substrate platform 210 has a doping concentration between about $10^{10}$ atoms/cm³ and about $10^{20}$ atoms/cm³, $10^{11}$ atoms/cm³ and about $10^{21}$ atoms/cm³, or about $10^{11}$ atoms/cm³ and about $10^{20}$ atoms/cm³. In various implementations, the substrate platform 210 can be doped with a dopant from the list of boron, phosphorous, arsenic, indium, gallium, antimony, bismuth, lithium, germanium, nitrogen, and gold.

In various implementations, the substrate platform 210 has a resistivity value between about $10^{-4}$ Ω-cm and about $10^{4}$ Ω-cm. In various implementations, the substrate platform 210 has a resistivity value between about $10^{-4}$ Ω-cm and about $10^{3}$ Ω-cm, about $10^{-3}$ Ω-cm and about $10^{3}$ Ω-cm, or about $10^{-3}$ Ω-cm and about $10^{4}$ Ω-cm.

As shown in FIG. 2A, the base plate 230 includes two serpentine arms 250 that extend outwards from the base plate 230 and are disposed radially evenly spaced from each other. In various implementations, the base plate 230 can include three serpentine arms, four serpentine arms, five serpentine arms, or any number of serpentine arms. According various implementations, the serpentine arms 250 extend outwards from the base plate 230 and are disposed radially evenly spaced from each other.

In various implementations, the serpentine arms 250 have a linear length along a path 252 at least about two times a separation distance (along a path 254) between the base plate 230 and the substrate platform 210. Note that the path 252 is indicated as a dashed-line that follows along the length of the serpentine arm 250, whereas the path 254 is indicated as the distance between the base plate 230 and the substrate platform 210 where the serpentine arm 250 are attached. In various implementations, the serpentine arms 250 have a linear length at least about three times, at least about four times, at least about 5 times, at least about 8 times, at least about 10 times, or at least about 15 times a separation distance between the base plate 230 and the substrate platform 210 and the linear length up to about 25 times, about 50 times, about 100 times, about 150 times, about 200 times, about 250 times, about 300 times, about 350 times, about 400 times, about 450 times, about 500 times, about 550 times, about 600 times, about 650 times, about 700 times, about 750 times, about 800 times, about 850 times, about 900 times, about 950 times, or about 1000 times, inclusive of any range in the linear length of separation distance between any two numbers described above.

In various implementations, the serpentine arms 250 include one of single crystal silicon, polycrystalline silicon, nanocrystalline silicon, amorphous silicon, or hydrogenated amorphous silicon. In various implementations, the serpentine arms 250 can include a metal, a metallic alloy, a ceramic, a composite, or a polymer. In various implementations, the serpentine arms 250 can include doped silicon, any allotrope of silicon, any inorganic glassy material or mixture, any inorganic polycrystalline material or mixture, any inorganic single crystalline material or mixture, any ceramic material comprising metal oxides, metalloid oxides, metal or metalloid nitrides, metal or metalloid oxides with nitrogen or other non-metalloid or metal elements, any doped combination of the above materials, any layered stack or structural combination of the above materials.

In various implementations, the serpentine arms 250 include a single layer of materials. In various implementations, the serpentine arms 250 include a composite material having multiple layers. In various implementations, the serpentine arms 250 can include an empty void layer, or one or more voids in the composite material.

In various implementations, the serpentine arms 250 have a thickness between about 0.001 μm and about 10 mm. In various implementations, the serpentine arms 250 have a thickness between about 0.01 μm and about 1 mm, about 0.01 μm and about 500 μm, about 0.01 μm and about 100 μm, about 0.01 μm and about 75 μm, about 0.01 μm and about 50 μm, about 0.01 μm and about 25 μm, about 0.01 μm and about 10 μm, about 0.1 μm and about 10 μm, about 0.1 μm and about 25 μm, about 0.1 μm and about 50 μm, about 0.1 μm and about 75 μm, about 0.1 μm and about 100 μm, about 0.1 μm and about 250 μm, about 0.1 μm and about 500 μm, or about 0.1 μm and about 1 mm, inclusive of any thickness ranges therebetween.

In various implementations, the serpentine arms 250 have a doping concentration between about $10^{10}$ atoms/cm$^3$ and about $10^{21}$ atoms/cm$^3$. In various implementations, the serpentine arms 250 have a doping concentration between about $10^{10}$ atoms/cm$^3$ and about $10^{20}$ atoms/cm$^3$, $10^{11}$ atoms/cm$^3$ and about $10^{21}$ atoms/cm$^3$, or about $10^{11}$ atoms/cm$^3$ and about $10^{20}$ atoms/cm$^3$. In various implementations, the serpentine arms 250 can be doped with a dopant from the list of boron, phosphorous, arsenic, indium, gallium, antimony, bismuth, lithium, germanium, nitrogen, and gold.

In various implementations, the serpentine arms 250 are configured to be flexible, for example, for bending without plastic deformation, material fatigue, and fracture in the serpentine arms 250 after repeated movements. In various implementations, the serpentine arms 250 are configured to support mechanical vibrations of the base plate 230. In various implementations, the serpentine arms 250 are fabricated from the same material layer as the base plate 230. In various implementations, the serpentine arms 250 have the same electrical properties, for example, electrical resistance and impedance as the base plate 230.

In various implementations, the serpentine arms 250 have a resistivity value between about $10^{-4}$ Ω-cm and about $10^4$ Ω-cm. In various implementations, the serpentine arms 250 have a resistivity value between about $10^{-4}$ Ω-cm and about $10^3$ Ω-cm, about $10^{-3}$ Ω-cm and about $10^3$ Ω-cm, or about $10^{-3}$ Ω-cm and about $10^4$ Ω-cm.

In various implementations, the base plate 230 and the substrate platform 210 are concentric. In various implementations, the base plate 230 is inside the substrate platform 210. In other words, the base plate 230 is suspended from the substrate platform 210 via the serpentine arms 250, as shown in FIG. 2A.

As shown in FIG. 2A, the base plate 230 is a square shape plate or a rectangular shape plate. In various implementations, the base plate 230 has a shape consisting of circular, oval, square, rectangle, pentagon, or hexagon.

In various implementations, the base plate 230 has a lateral dimension between about 100 nm and about 10 cm. In various implementations, the base plate has a lateral dimension between about 1 μm and about 1 cm, about 1 μm and about 1 mm, about 1 μm and about 800 μm, about 1 μm and about 600 μm, about 1 μm and about 500 μm, about 1 μm and about 400 μm, about 1 μm and about 300 μm, about 1 μm and about 200 μm, about 1 μm and about 100 μm, about 5 μm and about 500 μm, about 10 μm and about 500 μm, about 25 μm and about 500 μm, about 50 μm and about 500 μm, or about 100 μm and about 500 μm, inclusive of all dimensions therebetween.

In various implementations, the base plate 230 moves from the resting position for a distance between about 0.1 nm and about 10 mm. In various implementations, the base plate 230 moves from the resting position for a distance between about 1 nm and about 8 mm, about 1 nm and about 1 mm, about 10 nm and about 6 mm, about 100 nm and about 5 mm, about 1 μm and about 4 mm, about 1 μm and about 3 mm, about 1 μm and about 2 mm, about 1 μm and about 1 mm, about 10 μm and about 1 mm, about 25 μm and about 1 mm, about 50 μm and about 1 mm, or about 50 μm and about 2 mm, inclusive of any distance ranges therebetween.

In various implementations, the base plate 230 moves from the resting position for static displacement of a distance between about 1 nm and about 10 mm. In various implementations, the base plate 230 moves from the resting position for dynamic displacement of a distance between about 0.1 nm and about 100 μm. In various implementations, the base plate 230 is actuated in a static manner while concurrently having a superimposed vibrational dynamic movement. In various implementations, the dynamic movement of the base plate 230 is configured for sensing or measuring applications such as, for example, to facilitate modulation of payload release kinetics via agitation enhanced diffusion, or other kinetic actions as may be desirable.

In various implementations, the base plate 230 has a thickness between about 0.001 mm and about 10 mm. In various implementations, the base plate 230 has a thickness between about 0.01 μm and about 1 mm, about 0.01 μm and about 500 μm, about 0.01 μm and about 100 μm, about 0.01 μm and about 75 μm, about 0.01 μm and about 50 μm, about 0.01 μm and about 25 μm, about 0.01 μm and about 10 μm, about 0.1 μm and about 10 μm, about 0.1 μm and about 25 μm, about 0.1 μm and about 50 μm, about 0.1 μm and about 75 μm, about 0.1 μm and about 100 μm, about 0.1 μm and about 250 μm, about 0.1 μm and about 500 μm, or about 0.1 μm and about 1 mm, inclusive of any thickness ranges therebetween.

In various implementations, the base plate 230 has a first thickness and the substrate platform has a second thickness. In various implementations, the first thickness differs from the second thickness.

In various implementations, the base plate 230 includes one of single crystal silicon, polycrystalline silicon, nanocrystalline silicon, amorphous silicon, or hydrogenated amorphous silicon. In various implementations, the base plate 230 can include a metal, a metallic alloy, a ceramic, a composite, or a polymer. In various implementations, the base plate 230 can include doped silicon, any allotrope of silicon, any inorganic glassy material or mixture, any inorganic polycrystalline material or mixture, any inorganic single crystalline material or mixture, any ceramic material comprising metal oxides, metalloid oxides, metal or metalloid nitrides, metal or metalloid oxides with nitrogen or other non-metalloid or metal elements, any doped combination of the above materials, any layered stack or structural combination of the above materials.

In various implementations, the base plate 230 is a single layer of materials. In various implementations, the base plate 230 is a composite material having multiple layers. In various implementations, the base plate 230 can include an empty void layer, or one or more voids in the composite material.

In various implementations, the base plate 230 has a doping concentration between about $10^{10}$ atoms/cm$^3$ and about $10^{21}$ atoms/cm$^3$. In various implementations, the base plate 230 has a doping concentration between about $10^{10}$ atoms/cm$^3$ and about $10^{20}$ atoms/cm$^3$, $10^{11}$ atoms/cm$^3$ and about $10^{21}$ atoms/cm$^3$, or about $10^{11}$ atoms/cm$^3$ and about $10^{20}$ atoms/cm$^3$. In various implementations, the base plate 230 can be doped with a dopant from the list of boron, phosphorous, arsenic, indium, gallium, antimony, bismuth, lithium, germanium, nitrogen, and gold.

In various implementations, the base plate 230 has a resistivity value between about $10^{-4}$ Ω-cm and about $10^4$ Ω-cm. In various implementations, the base plate 230 has a resistivity value between about $10^{-4}$ Ω-cm and about $10^3$ Ω-cm, about $10^{-3}$ Ω-cm and about $10^3$ Ω-cm, or about $10^{-3}$ Ω-cm and about $10^4$ Ω-cm.

In various implementations, an electrical impedance across the base plate 230 and the substrate platform 210 is between about $10^2$Ω and about $10^{12}$Ω. In various implementations, an electrical impedance across the base plate 230 and the substrate platform 210 is between about $10^2$Ω and about $10^{11}$Ω, about $10^2$Ω and about $10^{10}$Ω, about $10^2$Ω and about $10^9$Ω, about $10^2$Ω and about $10^8$Ω, about $10^3$Ω and about $10^8$Ω, about $10^3$Ω and about $10^9$Ω, about $10^3$Ω and about $10^{10}$Ω, about $10^3$Ω and about $10^{11}$Ω, or about $10^3$Ω and about $10^{12}$Ω, inclusive of any impedance ranges therebetween.

In various implementations, the sharp member 260 is a needle, a microneedle, nanoneedle, a nanotube, a pillar, a micropillar, a nanopillar, or any physical projection with an aspect ratio of height to diameter of about 2 to about 1,000,000. In various implementations, the sharp member 260 has an aspect ratio of height to diameter of about 1 to about 1,000,000, about 1 to about 500,000, about 1 to about 100,000, about 1 to about 50,000, about 1 to about 10,000, about 1 to about 5,000, about 1 to about 1,000, about 1 to about 900, about 1 to about 800, about 1 to about 700, about 1 to about 600, about 1 to about 500, about 1 to about 400, about 1 to about 300, about 1 to about 200, about 1 to about 100, about 1 to about 90, about 1 to about 80, about 1 to about 70, about 1 to about 60, about 1 to about 50, about 1 to about 40, about 1 to about 30, about 1 to about 20, about 1 to about 10, about 1 to about 9, about 1 to about 8, about 1 to about 7, about 1 to about 6, about 1 to about 5, about 1 to about 4, about 1 to about 3, about 1 to about 2, about 10 to about 1,000,000, about 10 to about 500,000, about 10 to about 100,000, about 10 to about 50,000, about 10 to about 10,000, about 10 to about 5,000, about 10 to about 1,000, about 10 to about 900, about 10 to about 800, about 10 to about 700, about 10 to about 600, about 10 to about 500, about 10 to about 400, about 10 to about 300, about 10 to about 200, about 10 to about 100, about 10 to about 90, about 10 to about 80, about 10 to about 70, about 10 to about 60, about 10 to about 50, about 10 to about 40, about 10 to about 30, about 10 to about 20, or about 5 to about 20, inclusive of any aspect ratio ranges therebetween.

In various implementations, the sharp member 260 includes insulating materials, such as silicon oxide or silicon nitride, or other metallic oxides, such as hafnium or aluminum oxide. In various implementations, the sharp member 260 is coated with a coating for chemical inertness and/or electrical insulation. In various implementations, the coating can be either deposited via a vapor phase or liquid phase deposition technique. In various implementations, the coating includes coating materials, such as for example, inorganic insulators, such as oxides or nitrides, and various polymers that can be deposited or polymerized in-situ. In various implementations, the coating includes for example, a vapor phase deposited polymer coating, such as Parylene. In various implementations, the coating can also include materials that modify the surface properties or provide reactive groups for attaching molecules. These include the organosilanes, such as alkyl silanes, dichloro or trichloro silanes or trimethoxy silanes, fluorinated alkyl silanes, and silanes with reactive groups designed to change the surface properties such as aminosilanes, and methoxy or ethoxy silanes. Another category of coatings that can be applied in a liquid phase are those used in electrophoresis, such as polyacrylamides, polydimethylacrylamide, agarose, and other polysaccharides, such as guaran or locust bean gum. Yet another category of surface coatings can include surfactant molecules, in particular nonionic surfactants, such as Pluronic, a triblock copolymer with polypropylene oxide and polyethylene oxide segments. In various implementations, the coatings include multiple layers of coatings to help achieve various goals, such as an electrically insulating layer followed by a layer to promote molecular binding. In various implementations, the coating on the sharp member 260 is to help facilitate binding of certain chemicals to be inserted into a cell.

In various implementations, the coating can be any material suitable for providing chemical inertness, electrical insulation, and/or fluid wettability (e.g., for contact angle control). In various implementations, the coating can include, for example, a hydrophilic coating that includes a range of material classes, including for example, any small molecule, proteins, peptides, peptoids, polymers, or inorganic material, such as silicon, alumina, a ceramic, gold, silicon oxide, a metal, a polymer, a layered stack of these materials, of/or any combination either physically absorbed and/or deposited, or chemically bound covalently or non-covalently. In various implementations, the coating can include, for example, a hydrophobic coating that has a contact angle between about 95° and about 165°. In various implementations, the hydrophobic coating has a contact angle between about 95° and about 165°, between about 100° and about 165°, about 105° and about 165°, about 110° and about 165°, about 120° and about 165°, about 95° and about 150°, about 95° and about 140°, or about 95° and about 130°, inclusive of any contact angle ranges therebetween.

In various implementations, the hydrophilic coating has a contact angle between about 20° and about 80°. In various implementations, the hydrophilic coating has a contact angle between about 25° and about 80°, about 30° and about 80°, about 35° and about 80°, about 40° and about 80°, about 20° and about 70°, about 20° and about 60°, or about 20° and about 50°, inclusive of any contact angle ranges therebetween.

In various implementations, the sharp member 260 has a combination of patterned hydrophilic and hydrophobic coatings. The hydrophobic coating can include a variety of classes such as azides, organosilanes, hydrocarbons, or fluorocarbons, or organic molecules covalently bound or non-covalently bound. In various implementations, the coating on the sharp member 260 is to help facilitate binding of certain chemicals to be inserted into a cell.

In various implementations, the sharp member 260 has a length between about 50 nm and about 1 mm. In various implementations, the sharp member 260 has a length between about 1 μm and about 1 mm, about 1 μm and about 500 μm, about 1 μm and about 250 μm, about 1 μm and about 100 μm, about 1 μm and about 75 μm, about 1 μm and about 50 μm, about 2 μm and about 50 μm, about 2 μm and about 75 μm, about 2 μm and about 100 μm, about 2 μm and about 250 μm, about 2 μm and about 500 μm, or about 2 μm and about 1 mm, inclusive of any length ranges therebetween.

In various implementations, the structure 200 can include a plurality of sharp members 260 up to about 5 sharp members, up to about 10 sharp members, up to about 50 sharp members, up to about 100 sharp members, up to about 500 sharp members, up to about 1,000 sharp members, up to about 5,000 sharp members, up to about 10,000 sharp members, up to about 50,000 sharp members, up to about 100,000 sharp members, up to about 500,000 sharp members, up to about 1,000,000 sharp members, up to about 5,000,000 sharp members, up to about 10,000,000 sharp members, up to about 50,000,000 sharp members, up to about 100,000,000 sharp members, or up to about 500,000,000 sharp members, inclusive of any ranges of sharp members between any two numbers described above. In various implementations, the base plate 230 can accommodate a plurality of sharp members 260 up to about 5 sharp members, up to about 10 sharp members, up to about 50 sharp members, up to about 100 sharp members, up to about 500 sharp members, up to about 1,000 sharp members, up to about 5,000 sharp members, up to about 10,000 sharp members, up to about 50,000 sharp members, up to about 100,000 sharp members, up to about 500,000 sharp members, up to about 1,000,000 sharp members, up to about 5,000,000 sharp members, up to about 10,000,000 sharp members, up to about 50,000,000 sharp members, up to about 100,000,000 sharp members, or up to about 500,000,000 sharp members, inclusive of any ranges of sharp members between any two numbers described above.

In various implementations, the structure 200 includes a plurality of base plates 230.

In various implementations, the structure 200 further includes a counter-electrode 280 disposed parallel to the base plate 230 (the electrode). In various implementations, the counter-electrode 280 is suspended above the base plate 230 near the sharp member 260. In various implementations, the counter-electrode 280 is disposed below the base plate 230 in the pit 212. In various implementations, the structure 200 includes two separately or commonly addressable counter-electrodes above the base plate 230 near the sharp member 260. In various implementations, the structure 200 includes two separately or commonly addressable counter-electrodes below the base plate 230 in the pit 212. In various implementations, the structure 200 includes a counter-electrode above the base plate 230 near the sharp member 260 and a counter-electrode below the base plate 230 in the pit 212. In various implementations, the counter-electrodes can be of differing thicknesses, morphology, geometry, material, resistance, impedance, optical transparence, or any combination thereof. In various implementations, the counter-electrode geometry can be varied, bifurcated, trifurcated, or generally segmented, with separate segments individually addressed. In various implementations, the segmenting addressability of base plates allows for lateral correction in the pitch of the sharp member and/or out of plane angle tilt correction (for cases where nanofabrication defects need active correction during use). This is implemented by varying the voltages on each counter electrode segment to create a differential out of plane (z-axis) force between the needle platform and the counter electrode, as will be shown below in FIG. 6B. In various implementations, the based plate 230 (the electrode) and the counter-electrode have a separation distance between about 1 μm and about 1 mm, about 1 μm and about 500 μm, about 1 μm and about 250 μm, about 1 μm and about 100 μm, about 1 μm and about 75 μm, about 1 μm and about 50 μm, about 2 μm and about 50 μm, about 2 μm and about 75 μm, about 2 μm and about 100 μm, about 2 μm and about 250 μm, about 2 μm and about 500 μm, or about 2 μm and about 1 mm, inclusive of any separation distance ranges therebetween.

In various implementations, the counter-electrode 280 has a thickness between about 0.001 μm and about 10 mm. In various implementations, the counter-electrode 280 has a thickness between about 0.01 μm and about 1 mm, about 0.01 μm and about 500 μm, about 0.01 μm and about 100 μm, about 0.01 μm and about 75 μm, about 0.01 μm and about 50 μm, about 0.01 μm and about 25 μm, about 0.01 μm and about 10 μm, about 0.1 μm and about 10 μm, about 0.1 μm and about 25 μm, about 0.1 μm and about 50 μm, about 0.1 μm and about 75 μm, about 0.1 μm and about 100 μm, about 0.1 μm and about 250 μm, about 0.1 μm and about 500 μm, or about 0.1 μm and about 1 mm, inclusive of any thickness ranges therebetween.

In various implementations, the counter-electrode 280 includes one of single crystal silicon, polycrystalline silicon, nanocrystalline silicon, amorphous silicon, or hydrogenated amorphous silicon. In various implementations, the counter-electrode 280 can include a metal, a metallic alloy, a ceramic, a composite, or a polymer. In various implementations, the counter-electrode can include doped silicon, any allotrope of silicon, any inorganic glassy material or mixture, any inorganic polycrystalline material or mixture, any inorganic single crystalline material or mixture, any ceramic material comprising metal oxides, metalloid oxides, metal or metalloid nitrides, metal or metalloid oxides with nitrogen or other non-metalloid or metal elements, any doped combination of the above materials, any layered stack or structural combination of the above materials. In various implementations, the counter-electrode 280 can include indium-tin oxide (ITO), titanium nitride (TiN), a metal film, a doped semiconducting film, an inorganic semiconductor, a composite, an organic conducting film, any carbon allotrope including various types of graphene, a graphene oxide, mismatched graphene, and any combination thereof.

In various implementations, the counter-electrode 280 is a single layer of materials. In various implementations, the counter-electrode 280 is a composite material having multiple layers. In various implementations, the counter-electrode 280 can include an empty void layer, or one or more voids in the composite material.

In various implementations, the counter-electrode 280 has a doping concentration between about $10^{10}$ atoms/cm$^3$ and about $10^{21}$ atoms/cm$^3$. In various implementations, the counter-electrode 280 has a doping concentration between about $10^{10}$ atoms/cm$^3$ and about $10^{20}$ atoms/cm$^3$, $10^{11}$ atoms/cm$^3$ and about $10^{21}$ atoms/cm$^3$, or about $10^{11}$ atoms/cm$^3$ and about $10^{20}$ atoms/cm$^3$. In various implementations, the counter-electrode 280 can be doped with a dopant from the list of boron, phosphorous, arsenic, indium, gallium, antimony, bismuth, lithium, germanium, nitrogen, and gold.

In various implementations, the counter-electrode 280 has a resistivity value between about $10^{-4}$ Ω-cm and about $10^{4}$ Ω-cm. In various implementations, the counter-electrode 280 has a resistivity value between about $10^{-4}$ Ω-cm and about $10^{3}$ Ω-cm, about $10^{-3}$ Ω-cm and about $10^{3}$ Ω-cm, or about $10^{-3}$ Ω-cm and about $10^{4}$ Ω-cm.

According to various implementations, a power source (not shown) can be electrically connected to the base plate 230 or substrate platform 210 (the electrode) and to the counter-electrode 280 to provide an electric potential difference ($V_o$), e.g., a direct current (DC) voltage, between about 0.1 μV and 10 kV. In various implementations, the electrode and the counter-electrode are configured to receive an electric potential difference ($V_o$) between about 1 V and 100 V. In various implementations, the electrode and the counter-electrode are configured to receive an electric potential difference ($V_o$) between about 10 V and 50 V. In various implementations, the electrode (base plate 230 and/or substrate platform 210) and a plurality of counter electrodes are configured to receive voltage signals that can be superimposed, and varied between each of the electrode/counter electrodes.

According to various implementations, a power source (not shown) can be electrically connected to the base plate (the electrode) and the counter-electrode to provide an alternating current (AC) across the base plate (the electrode) and the counter-electrode to generate an oscillating electric field for sensing, impedance sensing, actuating or to conduct measurements.

In various implementations, the AC across the base plate (the electrode) and the counter-electrode is supplied at a voltage between about 50 mV and about 300 V. In various implementations, the AC across the base plate (the electrode) and the counter-electrode is supplied at a voltage between about 50 mV and about 50 V, about 250 mV and about 5 V, about 500 mV and about 50 V, about 750 mV and about 50 V, about 1 V and about 50 V, about 5 V and about 50 V, about 10 V and about 50 V, about 250 mV and about 40 V, about 250 mV and about 30 V, about 250 mV and about 20 V, about 250 mV and about 10 V, about 250 mV and about 8 V, about 250 mV and about 6 V, about 250 mV and about 5 V, about 300 mV and about 5 V, about 1 V and about 5 V, about 0 V and about 30 V, or about 0 V and about 300V, inclusive of any voltage ranges therebetween. It is noted that the voltage may be 0 V when the base plate is in its resting position.

In various implementations, the AC across the base plate (the electrode) and the counter-electrode is supplied at an oscillating frequency between about 1 Hz and about 1 THz. In various implementations, the AC across the base plate (the electrode) and the counter-electrode is supplied at an oscillating frequency between about 10 Hz and about 100 GHz, about 100 Hz and about 10 GHz, about 1 kHz and about 1 GHz, about 10 kHz and about 1 GHz, about 100 kHz and about 1 GHz, about 500 kHz and about 1 GHz, about 1 MHz and about 1 GHz, about 10 MHz and about 1 GHz, about 100 MHz and about 1 GHz, about 10 kHz and about 500 MHz, about 10 kHz and about 100 MHz, about 10 kHz and about 50 MHz, about 10 kHz and about 30 MHz, about 10 kHz and about 20 MHz, about 10 kHz and about 10 MHz, about 100 kHz and about 10 MHz, or about 500 kHz and about 10 MHz, or about 1 MHz and about 10 MHz, inclusive of any frequency ranges therebetween.

Figure 2B:
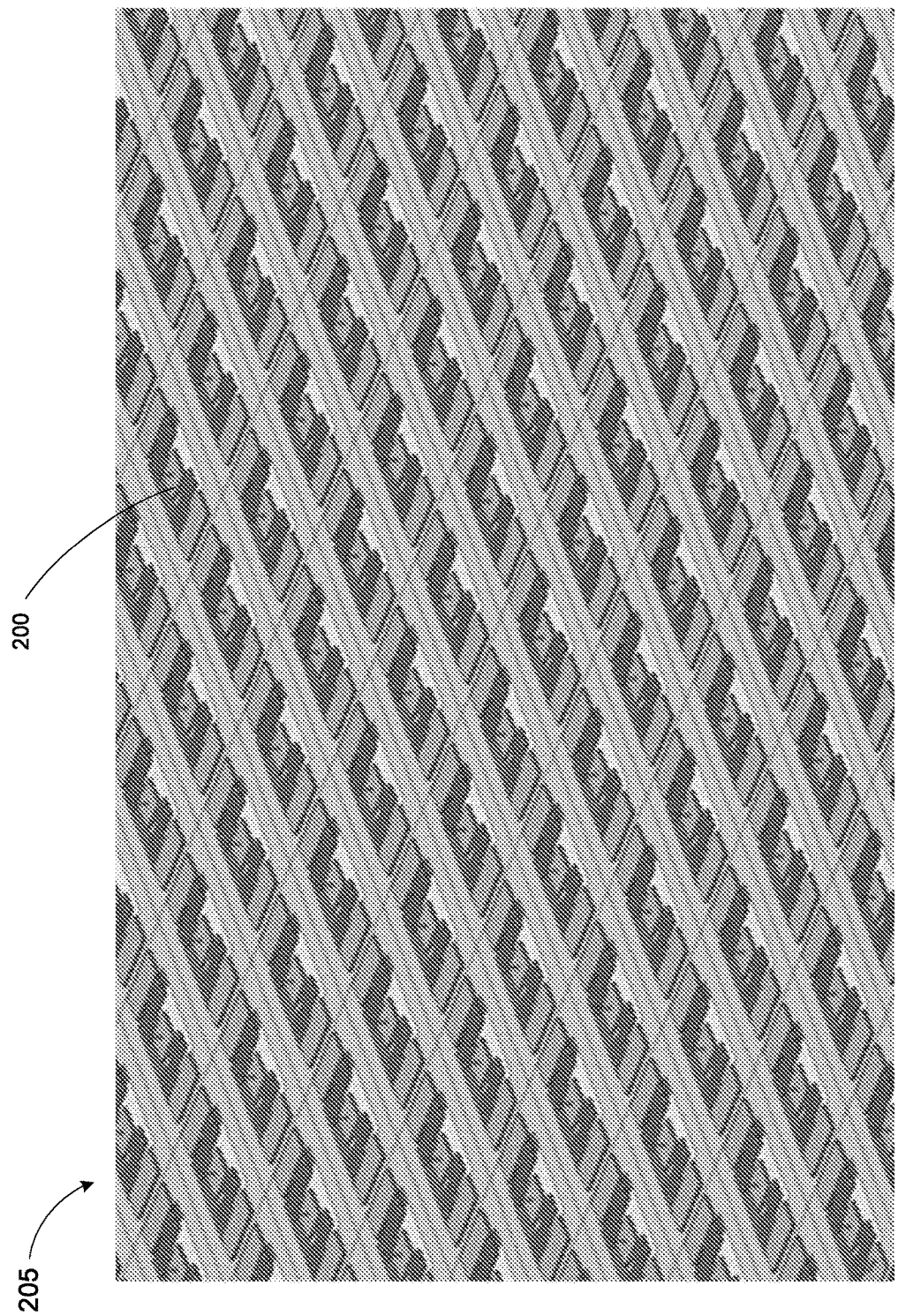
FIG. 2B shows a schematic view of an array of the example MEMS structures of FIG. 2A, according to various implementations.

FIG. 2B shows a schematic view of an array 205 of the example MEMS structures 200 of FIG. 2A, according to various implementations. As shown in FIG. 2B, the array 205 is a portion of a system that includes a plurality of the structures 200. In various implementations of the system, the plurality of structures 200 ranges from about 1 to about $10^8$ structures. According to various implementations, each of the structures 200 in the system includes a respective sharp member (or plurality of sharp members). In various implementations of the system, the plurality of structures 200 are separated from each other by between about 0.1 μm and 10 cm, about 0.1 μm and 1 cm, about 0.1 μm and 1 mm, about 0.1 μm and 500 μm, about 0.1 μm and 100 μm, by about 0.1 μm and 75 μm, about 0.1 μm and 50 μm, about 0.1 μm and 25 μm, about 0.1 μm and 10 μm, about 10 μm and 1 μm, or about 20 μm and 1 mm, inclusive of any separation distance ranges therebetween.

FIG. 3A shows a schematic top view of another example MEMS structure 300a having serpentine arms, according to various implementations. As shown in FIG. 3A, the structure 300a includes a substrate platform 310a and a circular base plate 330a having a plurality of serpentine arms 350a that are curved around the circular base plate 330a. As shown in FIG. 3A, the circular base plate 330a is attached to the substrate platform 310a via the plurality of curving serpentine arms 350a so that the base plate 330a is at a resting position. Unlike the structure 200 of FIG. 2A, the structure 300a is circular, and based on the circular base plate 330a, the curving serpentine arms 350a and the substrate platform 310a are designed to accommodate the circular base plate 330a to achieve a more compact design. As shown in FIG. 3A, a sharp member 360a is disposed substantially perpendicular to the plane of the circular base plate 330a. Similar to the structure 200, initially, the base plate 330a and the substrate platform 310a are co-planar. In various implementations, the circular base plate 330a is an electrode and is configured to move up or down away from the resting position based on electrostatic actuation in a direction perpendicular to the plane of the circular base plate 330a and the substrate platform 310a. Employing a plurality of serpentine arms 350a (rather than two serpentine arms as shown for example in FIG. 2A) minimizes rotational and out of plane movement of the base plate or needle platform 330a, and thus of the sharp member or needle 360a.

FIG. 3B shows a schematic top view of yet another example MEMS structure 300b having serpentine arms, according to various implementations. As shown in FIG. 3B, the structure 300b includes a substrate platform 310b and a circular base plate 330b having a plurality of serpentine arms 350b that are curved around the circular base plate 330b. As shown in FIG. 3A, the circular base plate 330b is attached to the substrate platform 310b via the plurality of curving serpentine arms 350b so that the base plate 330b is at a resting position. Unlike the structure 200 of FIG. 2A, and similar to the structure 300a of FIG. 3A, the structure 300b is circular, and based on the circular base plate 330b, the curving serpentine arms 350b and the substrate platform 310b are designed to accommodate the circular base plate 330b to achieve a more compact design. Unlike the structure 300a of FIG. 3A, the structure 300a includes a lightly larger circular base plate 330b, and accordingly, the curving serpentine arms 350b have larger widths and closer serpentine structures within the serpentine arms 350b. Assuming, for example, that substrate platform 310a and substrate platform 310b have substantially the same (or exactly the same) dimensions, since the circular base plate 330b is larger, it would be much closer to the substrate platform 310b, compared to the structure 300a of FIG. 3A. As a result, for this specific example, the separation distance for structure 300b would be less than the separation distance for structure 300a.

As shown in FIG. 3B, a sharp member 360b is disposed substantially perpendicular to the plane of the circular base plate 330b. Similar to the structure 200 and structure 300a, initially, the circular base plate 330b and the substrate platform 310b are co-planar. In various implementations, the circular base plate 330b is an electrode and is configured to move up or down away from the resting position based on electrostatic actuation in a direction perpendicular to the plane of the circular base plate 330b and the substrate platform 310b.

All other parameters, including material, physical, chemical and mechanical properties described with respect to the structure 300a of FIG. 3A and structure 300b of FIG. 3B are similar or substantially similar to those included in the structure 200 described with respect to FIG. 2A, and therefore, will not be provided in further detail.

Figure 3C:
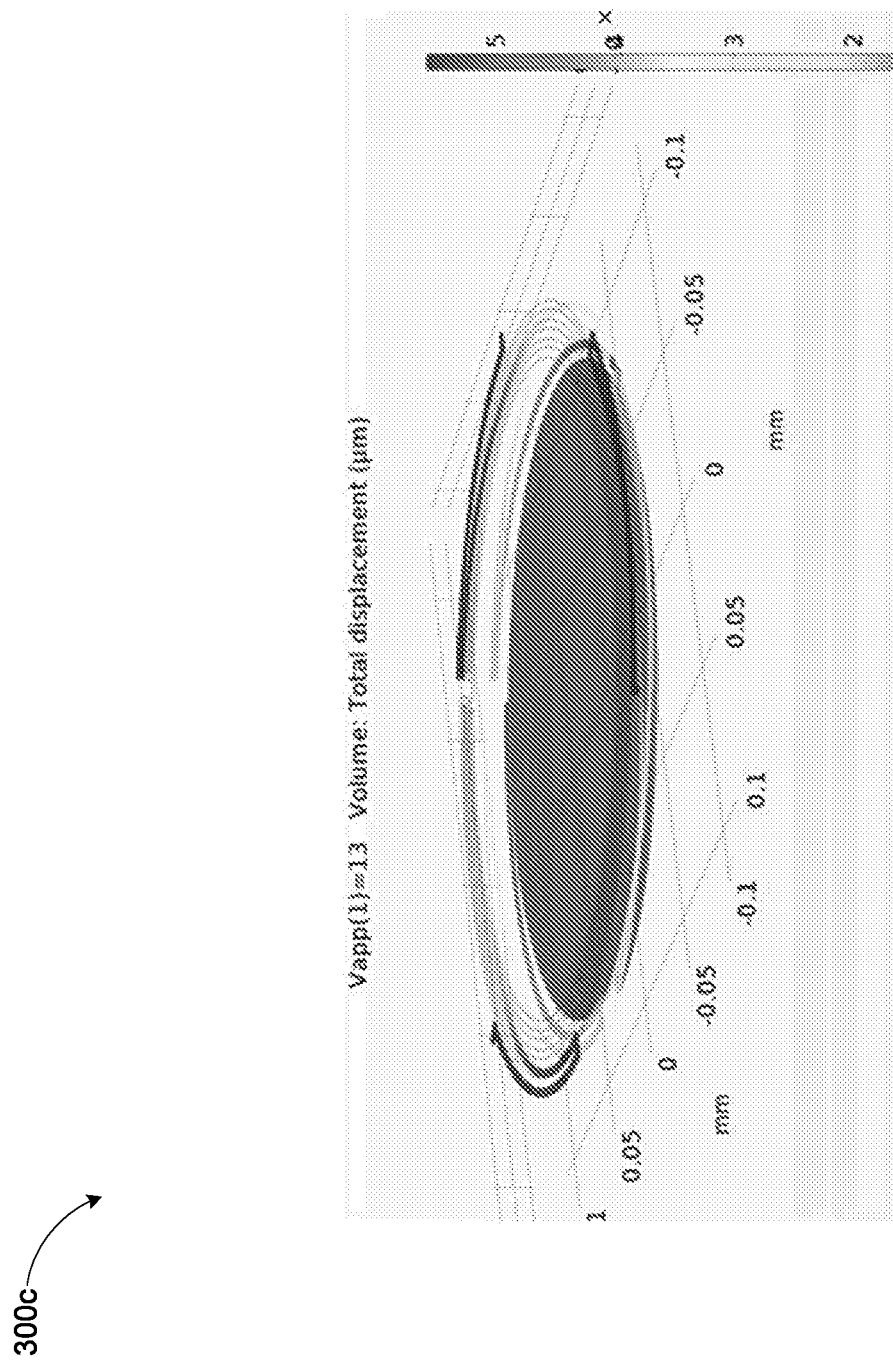
FIG. 3C is a graphical illustration showing simulation results of another serpentine cantilever structure being deflected.

FIG. 3C is a graphical illustration 300c showing simulation results of a serpentine cantilever structure being deflected. The illustration 300c shows the finite element simulation results of the deflection at an applied voltage of 13 V across the structure 300b and a counter-electrode (not shown in FIG. 3B). The simulation results are based on the counter-electrode disposed at a distance of about 20 μm away from the circulate base plate 330b, which is made of single crystal silicon having a thickness of 0.75 μm. As shown in the simulation, the deflection of the circular base plate 330b is about 5.6 μm.

Figure 3E:
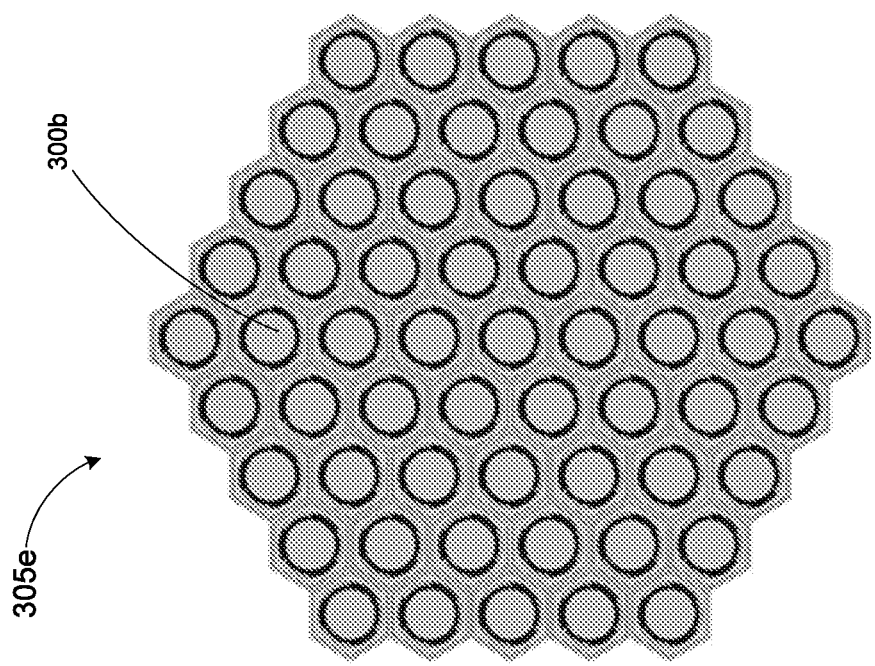
FIG. 3E shows a schematic view of an array of the example MEMS structures of FIG. 3B, according to various implementations.
Figure 3D:
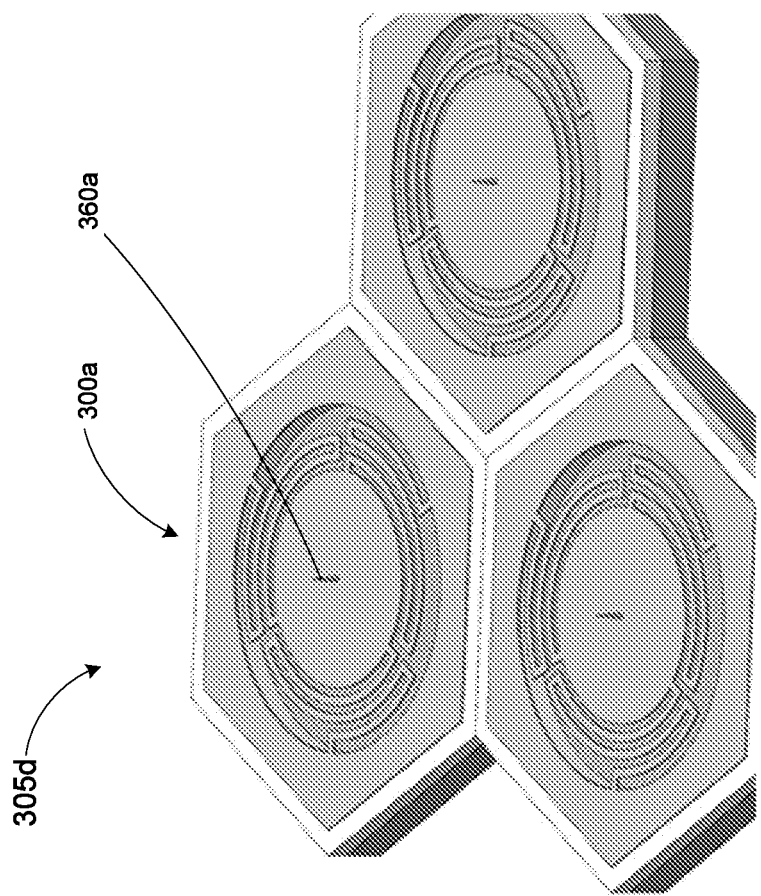
FIG. 3D shows a schematic view of an array of the example MEMS structures of FIG. 3A, according to various implementations.

FIG. 3D shows a schematic view of an array 305d of the example MEMS structures 300a of FIG. 3A, according to various implementations. As shown in FIG. 3D, the array 305d is a portion of a system that includes a plurality of the structures 300a that are arranged in a hexagonal tile. In various implementations of the system, the plurality of structures 300a ranges from about 1 to about $10^8$ structures. According to various implementations, each of the structures 300a in the system includes a respective sharp member 360a. In various implementations of the system, the plurality of structures 300a are separated from each other, e.g., center to center distance between two adjacent structures 300a, by about 0.1 μm and 10 cm, about 0.1 μm and 1 cm, about 0.1 μm and 1 mm, about 0.1 μm and 500 μm, about 0.1 μm and 100 μm, by about 0.1 μm and 75 μm, about 0.1 μm and 50 μm, about 0.1 μm and 25 μm, about 0.1 μm and 10 μm, about 10 μm and 1 mm, or about 20 μm and 1 mm, inclusive of any separation distance ranges therebetween.

Similarly, FIG. 3E shows a schematic view of an array 305e of the example MEMS structures 300b of FIG. 3B, according to various implementations. As shown in FIG. 3E, the array 305e is a portion of a system that includes a plurality of the structures 300b that are arranged in a hexagonal tile. In various implementations of the system, the plurality of structures 300b ranges from about 1 to about $10^8$ structures. According to various implementations, each of the structures 300b in the system includes a respective sharp member (not shown). In various implementations of the system, the plurality of structures 300b are separated from each other, e.g., center to center distance between two adjacent structures 300b, by about 0.1 μm and 10 cm, about 0.1 μm and 1 cm, about 0.1 μm and 1 mm, about 0.1 μm and 500 μm, about 0.1 μm and 100 μm, by about 0.1 μm and 75 μm, about 0.1 μm and 50 μm, about 0.1 μm and 25 μm, about 0.1 μm and 10 μm, about 10 μm and 1 mm, or about 20 μm and 1 mm, inclusive of any separation distance ranges therebetween. Within the needle platform of a given MEMS structure 300b, whether with multiple needles 360 or one needle 360, all the needles 360 may be addressed together if they are moved by the same platform 330. However, each device 300b of the array 305e may be able to move its needle platform 330 either in synchrony with, in a firing pattern with, or independently from, the movement of the needle platforms 330 in other devices 300b of the array 305e. In other words, multiple devices 300b of the array 305e may be multiplexed independently with different signals.

FIG. 4 is a flow chart for a method 400 of operating an example MEMS device having serpentine arms, according to an illustrative implementation. As shown in FIG. 4, the method 400 includes providing a power source at step 410. In various implementations, the power source is configured to generally provide an applied signal from a DC source, AC source, or combination of mixed signals or as a means of electrical/signal communication to an electrode/actuator. In various implementations, the power source is configured to apply a mixed signal (DC and AC signal component) as well as sensing of the output signal. In various implementations, a high-frequency signal is input to match appropriately to the impedance of an electrode/actuator. In various implementations, the high-frequency signal is superimposed on a DC component that causes the electrode/actuator to actuate. The high-frequency signal is temporally completely mismatched with the deflection kinetics of the electrode/actuator, however, as the actuator is deflected, the resistance and corresponding impedance of the material is altered due to differential atomic lattice spacing. In various implementations, the carrier mobility is altered by the materials deflection and so the impedance change may be measured in situ and correlated to a deflection value. In various implementations, this value can be recorded as a function of the applied DC voltage signal component via the instruction set. In various implementations, the readout is used to determine the real time displacement of the actuator.

The method 400 also includes providing the device having a substrate platform, an electrode having a plurality of serpentine arms, the electrode attached to the substrate platform via the plurality of serpentine arms, a sharp member disposed substantially perpendicularly on the electrode, and a counter-electrode disposed substantially parallel to the electrode at step 420. In various implementations, the electrode and the substrate platform are co-planar. In various implementations, the electrode is provided on a plane in a resting position, and configured to move in a direction perpendicular to the plane away from the resting position.

The method also includes supplying, via the power source, a direct current (DC) across the electrode and the counter-electrode of the device, thereby generating an electrostatic field across the electrode and the counter-electrode of the device at step 430.

In various implementations, the method 400 optionally includes supplying, via the power source, an electric potential difference ($V_o$) between about 0.1 μV and 10 kV across the electrode and the counter-electrode at step 440. In various implementations, the method 400 optionally includes supplying, via the power source, the direct current (DC) across each respective electrode and respective counter-electrode of the plurality of devices, thereby generating a plurality of electrostatic fields across each respective electrode and each respective counter-electrode of the plurality of devices at step 450. In some embodiments, the deflection of the base plate electrode (and therefore of the sharpened member attached to it) may optionally be estimated based on changing levels of impedance measured between the positive and negative leads of the power source. Although such estimation may not be required for the operation of the device, a knowledge of the base plate's deflection may be advantageous, for example, based on the size of the cells being injected, or to detect a misalignment or blockage of the sharp member or needle.

In various implementations, the electrode includes two serpentine arms that extend outwards from the electrode and are disposed radially evenly spaced from each other. In various implementations, the electrode includes three serpentine arms that extend outwards from the electrode and are disposed radially evenly spaced from each other. In various implementations, the electrode includes four serpentine arms that extend outwards from the electrode and are disposed radially evenly spaced from each other.

In various implementations, the serpentine arms have a linear length at least about two times a separation distance between the electrode and the substrate platform. In various implementations, the serpentine arms have a linear length at least about three times a separation distance between the electrode and the substrate platform. In various implementations, the serpentine arms have a linear length at least about four times a separation distance between the electrode and the substrate platform. In various implementations, the serpentine arms have a linear length at least about 5 times, at least about 8 times, at least about 10 times, or at least about 15 times a separation distance between the electrode and the substrate platform. In various implementations, the serpentine arms have a linear length up to about 1000 times a separation distance between the electrode and the substrate platform.

In various implementations, the electrode and the substrate platform are concentric. In various implementations, the electrode has a shape consisting of circular disc, oval, square, rectangle, pentagon, or hexagon. In various implementations, the electrode has a lateral dimension between about 100 nm and about 10 cm. In various implementations, the electrode has a lateral dimension between about 5 µm and about 500 µm.

In various implementations, the electrode moves from the resting position for a distance between about 0.1 nm and about 10 mm. In various implementations, the electrode moves from the resting position for a distance between about 1 nm and about 1 mm.

In various implementations, the electrode has a first thickness and the substrate platform has a second thickness. In various implementations, the first thickness differs from the second thickness. In various implementations, at least one of the electrode or the substrate platform has a thickness between about 0.001 µm and about 10 mm. In various implementations, at least one of the electrode or the substrate platform has a thickness between about 0.1 µm and about 10 µm.

In various implementations, at least one of the electrode or the substrate platform comprises one of single crystal silicon, polycrystalline silicon, nanocrystalline silicon, amorphous silicon, or hydrogenated amorphous silicon.

In various implementations, at least one of the electrode or the substrate platform has a doping concentration between about $10^{10}$ atoms/cm$^3$ and about $10^{21}$ atoms/cm$^3$. In various implementations, at least one of the electrode or the substrate platform has a doping concentration between about $10^{11}$ atoms/cm$^3$ and about $10^{20}$ atoms/cm$^3$. In various implementations, the at least one of the electrode or the substrate platform can be doped with a dopant from the list of boron, phosphorous, arsenic, indium, gallium, antimony, bismuth, lithium, germanium, nitrogen, and gold. In various implementations, at least one of the electrode or the substrate platform has a resistivity value between about $10^{-4}$ Ω-cm and about $10^4$ Ω-cm. In various implementations, at least one of the electrode or the substrate platform has a resistivity value between about $10^{-3}$ Ω-cm and about $10^3$ Ω-cm. In various implementations, an electrical impedance across the electrode and the substrate platform is between about $10^2$Ω and about $10^{12}$Ω. In various implementations, an electrical impedance across the electrode and the substrate platform is between about $10^3$Ω and about $10^8$Ω.

In various implementations, the sharp member has a length between about 50 nm and about 1 mm. In various implementations, the sharp member has a length between about 2 µm and about 50 µm.

In various implementations, the sharp member is a first sharp member, the device further includes a second sharp member. In various implementations, the device further includes a plurality of sharp members up to about 10 sharp members. In various implementations, the device further includes a plurality of sharp members up to about 100 sharp members. In various implementations, the device further includes a plurality of sharp members up to about 500,000,000 sharp members.

In various implementations, the electrode is a first electrode, the device further includes a second electrode. In various implementations, the device further includes a plurality of electrodes.

In various implementations, the counter-electrode has a thickness between about 0.01 µm and about 1 mm. In various implementations, the counter-electrode has a thickness between about 0.1 µm and about 10 µm.

In various implementations, the counter-electrode includes one of single crystal silicon, polycrystalline silicon, nanocrystalline silicon, amorphous silicon, or hydrogenated amorphous silicon.

In various implementations, the counter-electrode has a doping concentration between about $10^{10}$ atoms/cm$^3$ and about $10^{21}$ atoms/cm$^3$. In various implementations, the counter-electrode has a resistivity value between about $10^{-4}$ Ω-cm and about $10^4$ Ω-cm.

In various implementations, the method further includes supplying, via the power source, an electric potential difference ($V_o$) between about 0.1 µV and 10 kV across the electrode and the counter-electrode.

In various implementations, the method further includes supplying, via the power source, an electric potential difference ($V_o$) between about 1 V and 100 V across the electrode and the counter-electrode. In various implementations, the method further includes supplying, via the power source, an electric potential difference ($V_o$) between about 10 V and 50 V across the electrode and the counter-electrode.

In various implementations, the device is a first device, the method further includes a plurality of devices, and supplying, via the power source, the direct current (DC) across each respective electrode and respective counter-electrode of the plurality of devices to generate a plurality of electrostatic fields across each respective electrode and each respective counter-electrode of the plurality of devices.

In various implementations, the plurality of devices ranges from about 1 to about $10^8$ devices, each of the devices having a respective sharp member. In various implementations, the plurality of the devices are separated from each other by between about 0.1 µm and 10 cm.

Figure 5:
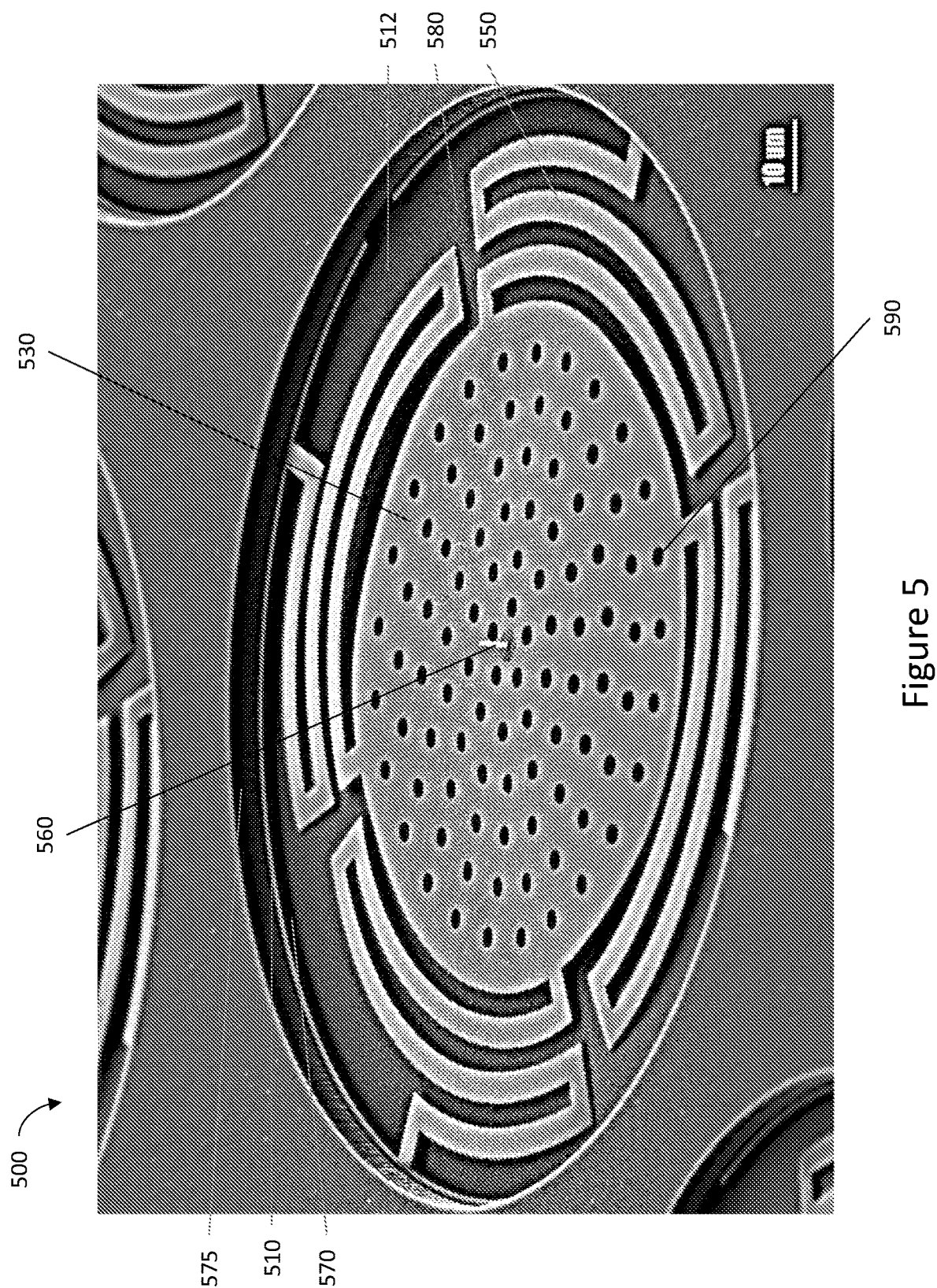
FIG. 5 is a perspective view of an example MEMS structure or MEMS device, according to various implementations.

FIG. 5 is a perspective view of an example MEMS structure or MEMS device 500, according to various implementations. Visible are the substrate platform 510, pit or cavity 512, base plate or needle platform 530, a plurality of serpentine arms 550, a sharp member 560 disposed on the base plate or needle platform 530, a bottom substrate 570, a top substrate 575, a bottom electrode or counter electrode 580, and a plurality of holes 590 disposed within the base plate or needle platform 530. These holes 590 can allow chemicals (e.g., etchants such as hydrofluoric acid) access to underlying layers of material during fabrication, so that, for example, a pit 512 can be formed in the bottom substrate 570, underneath the base plate or needle platform 530, after the base plate or needle platform 530 has been fabricated. Depending on the implementation, the holes 590 may be all the same size, or may be of different sizes, and may be spaced regularly in various patterns, or may be randomly spaced. In some embodiments, holes 590 may be created in a first manufacturing step, filled or covered in a second manufacturing step, and unfilled or uncovered in a third manufacturing step.

In some embodiments, the sharp member 560 is added to the platform during the manufacturing process. Example manufacturing steps for the sharp member may for example include: 1) Etch platform out of Si on SiO2. 2) Deposit Oxide to encapsulate platform. 3) Planarize. 4) Deposit thick poly-Si (needle material). 5) Etch poly-Si to form sharp member 560 and a trench around sharp member 560, down to the oxide encapsulated platform. 6) HF etch away sacrificial oxide. Other processes may be used instead or in addition to form the structure as shown.

Figure 6A:
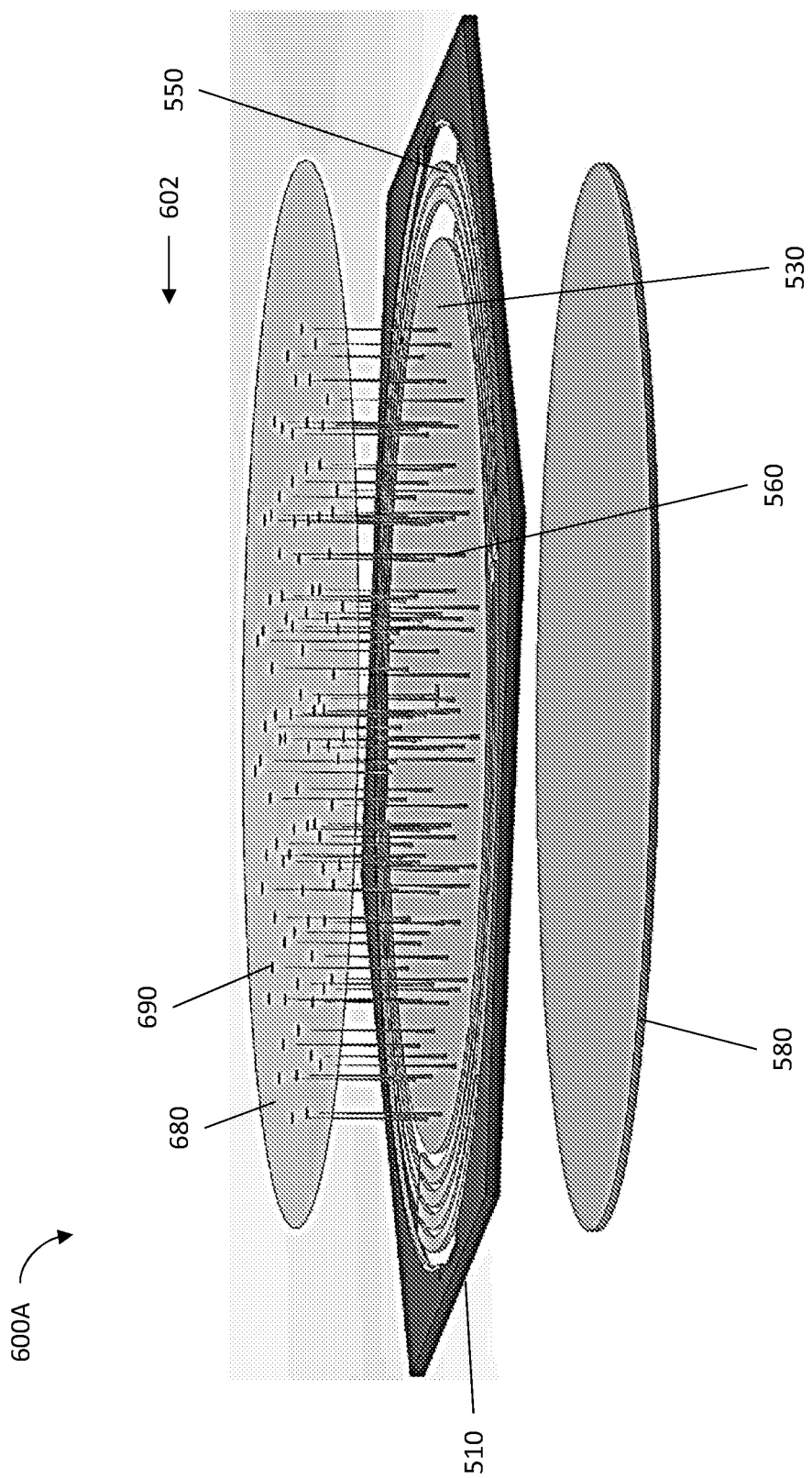
FIG. 6A is a perspective view of at least a portion of an example MEMS structure or MEMS device, according to various implementations.

FIG. 6A is a perspective view of at least a portion of an example MEMS structure or MEMS device 600A, according to various implementations. Visible are the substrate platform 510, a plurality of serpentine arms 550, and a base plate or needle platform 530. In the example shown in FIG. 6A, the base plate or needle platform 530 includes a plurality of sharp members or needles 560. As opposed to a single sharp member 560, a plurality of sharp members may contribute to higher throughput for the MEMS structure 600A by permitting a larger number of cells to be treated by a single device. Depending on the implementation, the sharp members or needles 560 may be substantially the same length, may vary in length according to a pattern, or may be of randomly distributed lengths.

Also visible are a bottom electrode (or counter electrode) 580 and a top electrode (or counter electrode or membrane) 680. The inclusion of electrodes both above and below the needle platform 530 permits the needle platform 530 to be pulled in both Z-directions (up and down), by varying the potential between the needle platform 530 and the two electrodes 580 and 680. This arrangement also allows for additional force sensing feedback control (e.g., by measuring impedance as described above), and tighter control over the movement of the needle platform.

In some embodiments, the top electrode 680 includes a plurality of holes or pore openings 690 aligned with the sharp members 560, such that if the base plate or needle platform 530 is deflected upward, the sharp members 560 are able to pass through the holes or pore openings 690. Such embodiments allow the multiple needles or sharp members 560 on a single needle platform 530 to enter the microfluidic region 602 above the top electrode 680. With a plurality of needles 560, it can be advantageous to have a plurality of associated pore openings 690 in the counter electrode or top electrode and membrane 680, aligned with the plurality of needles 560. With a single sharp member or needle 560, a single pore opening 690 may suffice to allow the sharp member or needle 560 access to the microfluidic region 602. Pore openings 690 may also be used to help align the needles 560, or to detect misalignment of the needles 560. For example, if the base platform 530 will not deflect upward past a certain height, this may indicate that the needles 560 and pores 690 are blocked or misaligned from one another.

Figure 6B:
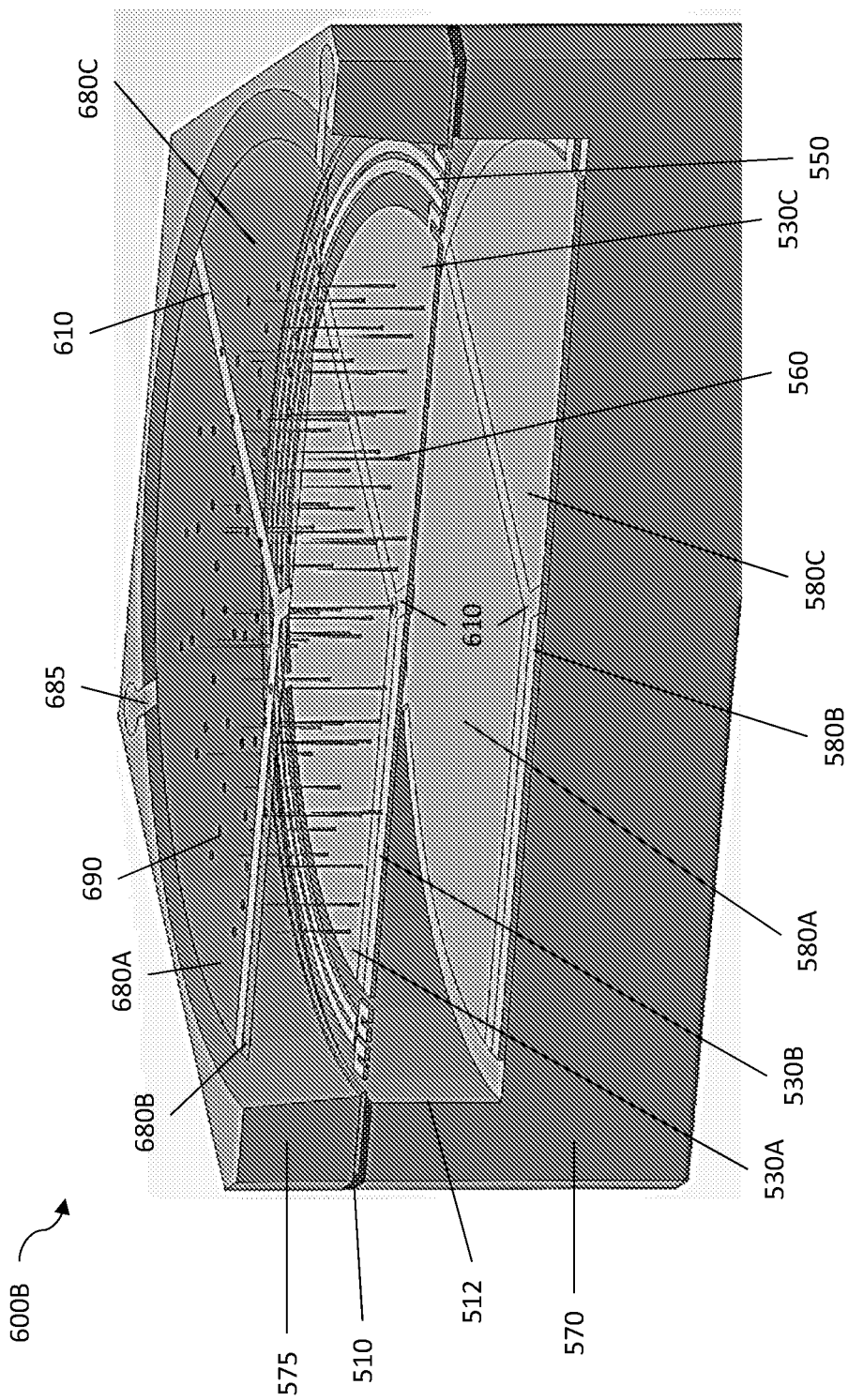
FIG. 6B is a cross-sectional perspective view of an example MEMS structure or MEMS device, according to various implementations.

FIG. 6B is a cross-sectional perspective view of an example MEMS structure or MEMS device 600B, according to various implementations. Visible are the bottom substrate 570 and top substrate 575, defining a pit 512 that projects completely through a thickness of the top substrate 575 and partly through a thickness of the bottom substrate 570. Sandwiched between the bottom substrate 570 and top substrate 575 is the substrate platform 510, from which project a plurality of serpentine arms 550 supporting the base plate or needle platform 530. In this example, the base plate or needle platform 530 is divided into three electrically isolated sections 530A, 530B, and 530C separated by a tripartite separator 610 that may serve as both a structural separator and an electrical insulator/isolator. Each section 530A, 530B, and 530C may be separately electrically addressed (e.g., through the corresponding serpentine arm 550 connecting that section). The base plate or needle platform 530 includes a plurality of sharp members 560.

Also visible is a bottom counter electrode 580, which is similarly divided into three electrically isolated, independently addressable sections 580A, 580B, and 580C, separated by a separator 610. Also visible is a top counter electrode 680 which includes a plurality of holes 690 aligned with the sharp members 560. The top counter electrode 680 is similarly divided into three independently addressable sections 680A, 680B, and 680C, separated by a tripartite separator 610. Because each section of the base plate 530, bottom counter-electrode 580, and top counter electrode 680 can be addressed independently, lateral as well as vertical forces can be created between the base plate 530 and the counter-electrodes 580 and 680. This arrangement allows for lateral positional correction as well as out of plane angle tilt correction. This is implemented for example by varying the voltages on each counter-electrode segment to create a differential out of plane (z-axis) force between the base plate or needle platform 530 and the counter electrodes 580 and 680. Such differential voltages can be applied between both the top and bottom counter electrodes, either concurrently or independently. In some embodiments, segments 530A, 530B, 530C, 580A, 580B, 580C, 680A, 680B, and 680C may each be bound and encapsulated in typically insulating material such as silicon dioxide (SiO2), dielectric materials such as hafnium oxide, SICOH, SiNx, tantalum oxide, aluminum oxide, zirconium oxide, lead zirconium titanate, barium titanate, a ceramic, a glass, plastics, or various metal or metalloid oxides. Similarly nitrides, carbides, or chalcogenides may be used in place of oxygen or in combination with the above mentioned metalloid or metal based insulating materials; for example tantalum nitride, tantalum selenide, aluminum nitride, zirconium carbide, or aluminum oxynitride.

Each segment may be addressed by an associated conductive arm 685, although any given conductive trace 685 may address either a single segment or else multiple segments to address, for example, out of plane correction. The segments can all be of the same material or, alternatively, at least two segments can be made of different materials. For example, each counter electrode segment 680A, 680B, 680C, 580A, 580B, 580C, may be independently addressed by voltage signals over an associated electrically conducting trace 685 and corresponding power supply, for example. In another example, each platform segment 530A, 530B, 530C may be independently addressed with a corresponding power supply signal supplied via the spatially associated and conductive or partially conductive serpentine arms. This intradevice multiplexed configuration allows for precise movement control, displacement feedback, as well as tilt and out of plane platform correction. These components may be comprised of materials similar to those listed above for the base platform. These materials may be functionally combined (layered or laterally segmented) with the insulating materials listed above, to provide, for example, the embodiment of FIG. 6B.

Although the MEMS device 600B is depicted in FIG. 6B as having three segments per layer and one conductive trace 685 per segment, other numbers of segments, numbers of conductive traces, numbers of segments per conductive trace, and number of conductive traces per segment may be employed instead or in addition, depending on the implementation. In some cases, each segment of a given platform 530 or counter electrode 580 or 680 may be considered a separate electrode or counter-electrode, such that a plurality of electrodes and/or counter-electrodes may be used to control the MEMS device 600B.

In some embodiments, the needle platform 530 can have a variable voltage while the voltage of the counter electrodes 580 and 680 remains constant. One advantage of such an arrangement is to limit interference with other electronic components (e.g., dielectrophoretic or DEP electrodes, not pictured) that may exist above, and close to, the top counter electrode or membrane 680. In some MEMS devices, the upper counter electrode or membrane 680 can be very close to a DEP electrode or other electronic component, whereas the needle platform 530 may be relatively more distant, creating less risk of electrical arcing or signal interference.

In some embodiments, each needle or group of needles 560 has a different voltage, or a few needles or groups of needles 560 have voltages applied or signals applied differently, in a multi-needle platform system. Variable signals can be supplied by locally associated serpentine arms 550.

Figure 7:
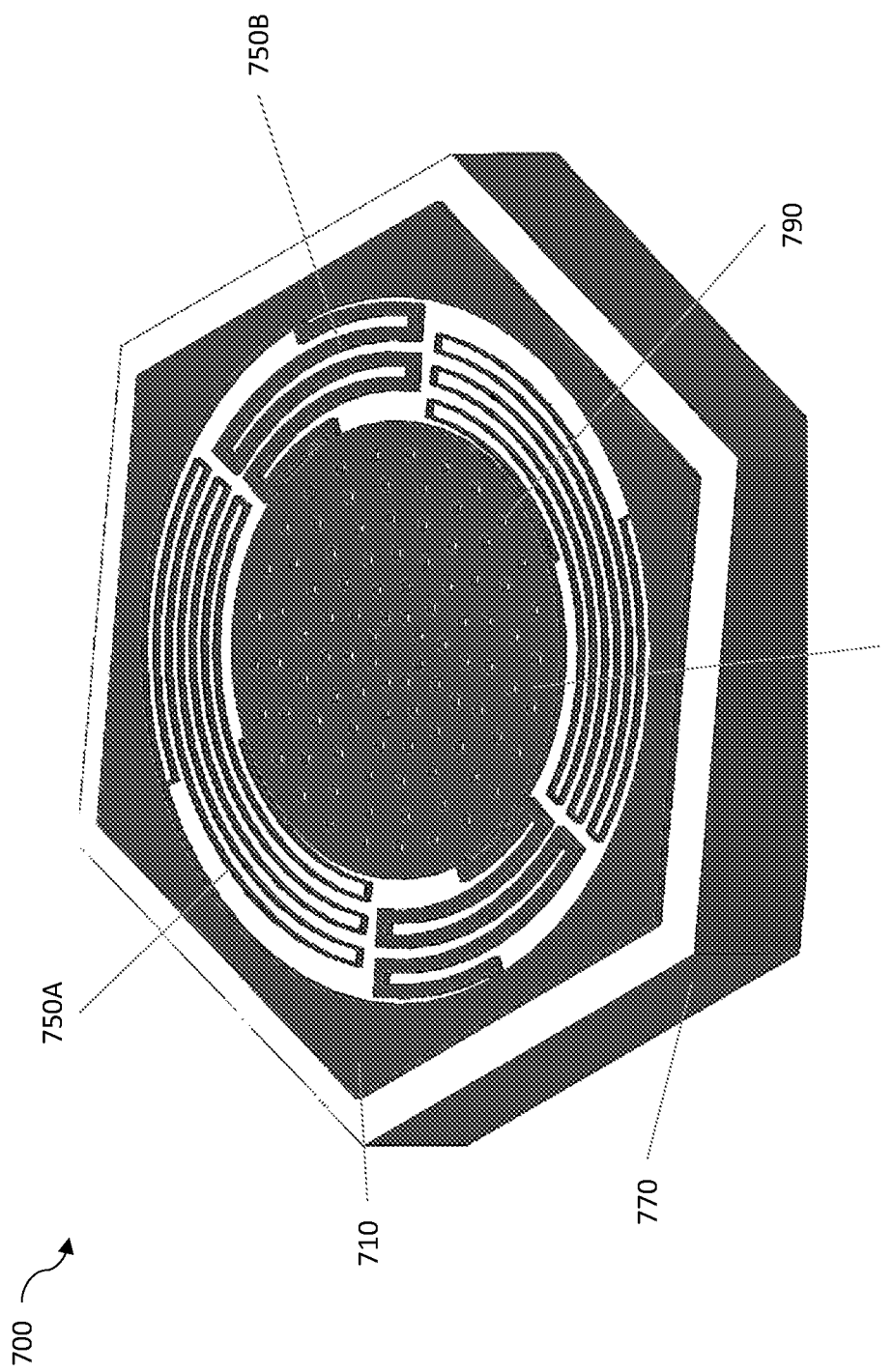
FIG. 7 is a top perspective view of an example MEMS structure or MEMS device, according to various implementations.

FIG. 7 is a top perspective view of an example MEMS structure or MEMS device 700, according to various implementations. Visible are the substrate 770, substrate platform 710, base plate or needle platform 730 that includes a plurality of holes 790 and supports at least one needle (not pictured), and two different types of serpentine arms, 750A and 750B that serve to connect the base plate 730 to, and suspend the base plate 730 from, the substrate platform 710. In the example shown in FIG. 7, the two serpentine arms 750A have a smaller cross-sectional area and a longer path length than the two serpentine arms 750B. This arrangement can be employed to limit rotational and out of plane movement of the base plate or needle platform 730, without increasing the overall stiffness of the plurality of serpentine arms for out of plane Z-axis movement of the base plate or needle platform 730. Although two types of serpentine arms 750A and 750B are shown, more or fewer different types may be employed instead or in addition. Serpentine corners may be sharp, 90-degree corners as shown, or may include other angles or rounded bends, depending on the implementation.

Figure 8:
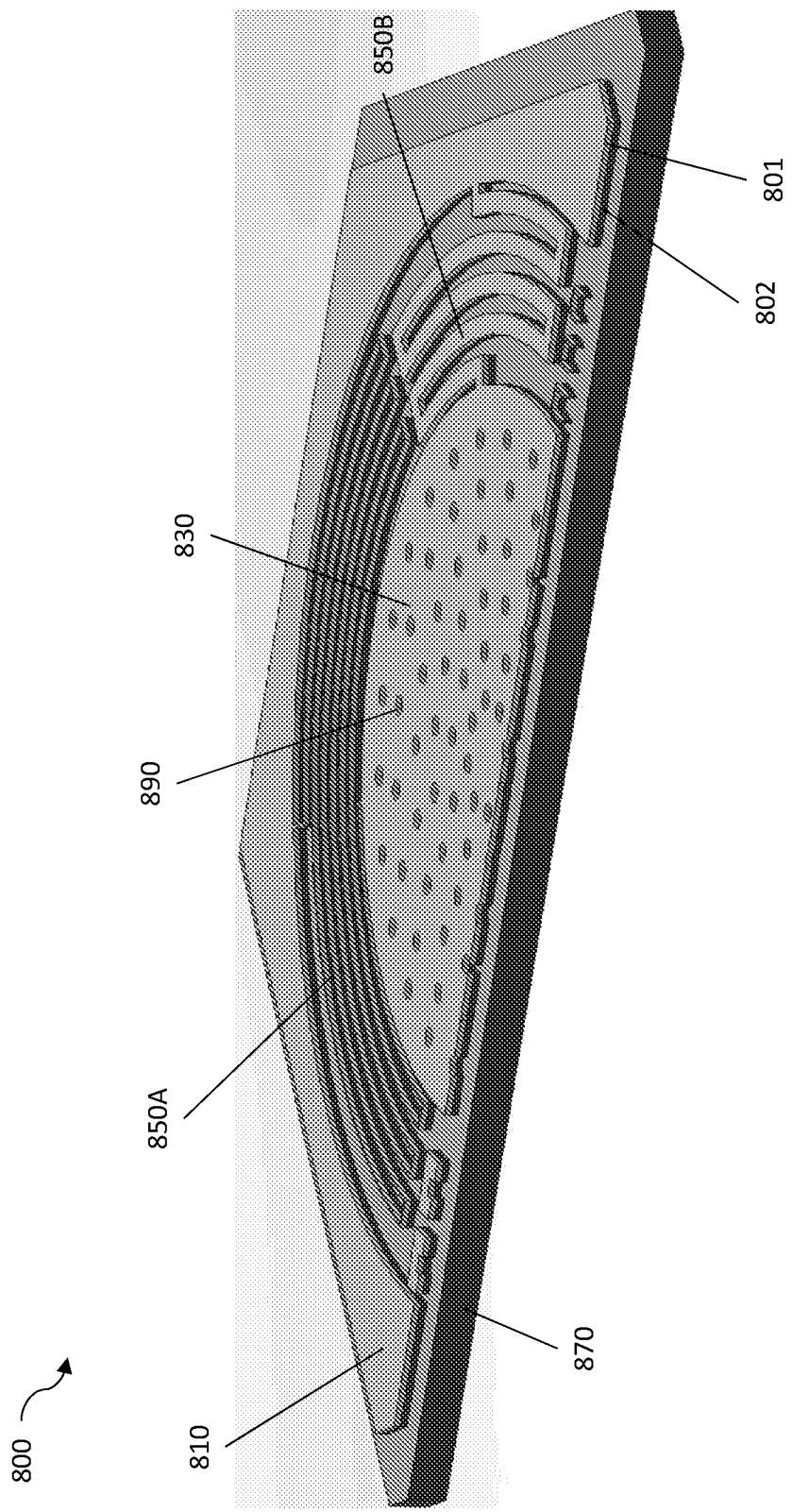
FIG. 8 is a cross-sectional perspective view of an example MEMS structure or MEMS device, according to various implementations.

FIG. 8 is a cross-sectional perspective view of an example MEMS structure or MEMS device 800, according to various implementations. Visible are the substrate 870, substrate platform 810, base plate or needle platform 830 that includes a plurality of holes 890 and supports at least one needle (not pictured), and two different types of serpentine arms, 850A and 850B. In this example, the substrate platform 810, base plate or needle platform 830, and serpentine arms 850A and 850B have been fabricated using two different material layers 801 and 802. There are many reasons that it might be desirable to have layering of different materials on the needle platform 830, including but not limited to electrical conductivity, electrical insulation or isolation, radio frequency shielding, structural reinforcement, stiffness enhancement, or flexibility enhancement.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

What is claimed is:

1. A device comprising:
   a substrate platform;
   a base plate having a plurality of serpentine arms, the base plate attached to the substrate platform via the plurality of serpentine arms, the base plate provided on a plane in a resting position; and
   a sharp member disposed on the base plate, the sharp member disposed substantially perpendicular to the plane,
   wherein the base plate and the substrate platform are co-planar, and
   wherein the base plate is configured to move in a direction perpendicular to the plane away from the resting position.

2. The device of claim 1, wherein the base plate comprises two serpentine arms that extend outwards from the base plate and are disposed radially evenly spaced from each other.

3. The device of claim 1, wherein the serpentine arms have a linear length at least about two times a separation distance between the base plate and the substrate platform.

4. The device of claim 1, wherein the base plate and the substrate platform are concentric.

5. The device of claim 1, wherein the base plate has a shape consisting of circular disc, oval, square, rectangle, pentagon, or hexagon.

6. The device of claim 1, wherein the base plate has a lateral dimension between about 100 nm and about 10 cm.

7. The device of claim 1, wherein the base plate moves from the resting position for a distance between about 0.1 nm and about 10 mm.

8. The device of claim 1, wherein the base plate has a first thickness and the substrate platform has a second thickness.

9. The device of claim 1, wherein at least one of the base plate or the substrate platform comprises one of single crystal silicon, polycrystalline silicon, nanocrystalline silicon, amorphous silicon, or hydrogenated amorphous silicon.

10. The device of claim 1, wherein at least one of the base plate or the substrate platform has a doping concentration between about $10^{10}$ atoms/cm$^3$ and about $10^{21}$ atoms/cm$^3$.

11. The device of claim 1, wherein at least one of the base plate or the substrate platform has a resistivity value between about $10^{-4}$ Ω-cm and about $10^4$ Ω-cm.

12. The device of claim 1, wherein an electrical impedance across the base plate and the substrate platform is between about $10^2$Ω and about $10^{12}$Ω.

13. The device of claim 1, wherein the sharp member has a length between about 50 nm and about 1 mm.

14. The device of claim 1, further comprising a plurality of sharp members disposed on the base plate up to about 500,000,000 sharp members.

15. The device of claim 1, wherein the base plate is an electrode and the device further comprises a counter-electrode disposed parallel to the electrode.

16. The device of claim 15, wherein the electrode and the counter-electrode are configured to receive an electric potential difference ($V_o$) between about 0.1 μV and 10 kV.

17. A method for operating a device comprising:
providing a power source;
providing the device comprising:
a substrate platform,
an electrode comprising a base plate having a plurality of serpentine arms, the electrode attached to the substrate platform via the plurality of serpentine arms,
a sharp member disposed substantially perpendicularly on the electrode, and
a counter-electrode disposed substantially parallel to the electrode;
supplying, via the power source, a direct current (DC) across the electrode and the counter-electrode of the device, thereby generating an electrostatic field across the electrode and the counter-electrode of the device.

18. The method of claim 17, further comprising:
supplying, via the power source, an electric potential difference ($V_o$) between about 0.1 μV and 10 kV across the electrode and the counter-electrode.

19. The method of claim 17, wherein the device is a first device, the method further comprising:
a plurality of devices; and
supplying, via the power source, the direct current (DC) across each respective electrode and respective counter-electrode of the plurality of devices, thereby generating a plurality of electrostatic fields across each respective electrode and each respective counter-electrode of the plurality of devices.

20. A device comprising:
a substrate platform;
a base plate electrode having a plurality of serpentine arms,
wherein the base plate electrode is attached to the substrate platform via the plurality of serpentine arms,
wherein the base plate electrode provided on a plane in a resting position, and
wherein the base plate electrode and the substrate platform are co-planar; and
a counter-electrode disposed parallel to, and non-coplanar with, the base plate electrode;
wherein the base plate electrode is configured to move in a direction perpendicular to the plane away from the resting position when a potential difference is applied between the base plate electrode and the counter-electrode.

* * * * *